(12) United States Patent
Swift et al.

(10) Patent No.: US 12,419,510 B2
(45) Date of Patent: Sep. 23, 2025

(54) SPECULUM

(71) Applicant: OBP Medical Corporation, Lawrence, MA (US)

(72) Inventors: Jeffrey Ralph Swift, Boca Grande, FL (US); Aaron J. Buchok, O'Fallon, MO (US)

(73) Assignee: CooperSurgical, Inc., Trumbull, CT (US)

( * ) Notice: Subject to any disclaimer, the term of this patent is extended or adjusted under 35 U.S.C. 154(b) by 86 days.

(21) Appl. No.: 18/225,345

(22) Filed: Jul. 24, 2023

(65) Prior Publication Data

US 2023/0363636 A1    Nov. 16, 2023

Related U.S. Application Data

(60) Division of application No. 16/515,371, filed on Jul. 18, 2019, now Pat. No. 11,744,454, which is a continuation of application No. 14/748,435, filed on Jun. 24, 2015, now Pat. No. 10,368,733, which is a continuation of application No. 14/316,787, filed on
(Continued)

(51) Int. Cl.
| | |
|---|---|
| *A61B 1/303* | (2006.01) |
| *A61B 1/00* | (2006.01) |
| *A61B 1/015* | (2006.01) |
| *A61B 1/06* | (2006.01) |

(Continued)

(52) U.S. Cl.
CPC ............ *A61B 1/32* (2013.01); *A61B 1/00032* (2013.01); *A61B 1/00066* (2013.01); *A61B 1/015* (2013.01); *A61B 1/0684* (2013.01); *A61B 1/07* (2013.01); *A61B 1/303* (2013.01); *A61B 1/0669* (2013.01)

(58) Field of Classification Search
CPC .............. A61B 1/32; A61B 1/07; A61B 1/303
See application file for complete search history.

(56) References Cited

U.S. PATENT DOCUMENTS

| 2,247,458 A | 7/1941 | Wintemberg |
| 3,324,850 A | 6/1967 | Gunning et al. |

(Continued)

FOREIGN PATENT DOCUMENTS

| CN | 201055387 | 5/2008 |
| CN | 102573700 | 12/2014 |

(Continued)

OTHER PUBLICATIONS

International Search Report of PCT/US2018/054925, Oct. 9, 2018.
(Continued)

*Primary Examiner* — Zade Coley
(74) *Attorney, Agent, or Firm* — Fish & Richardson P.C.

(57) ABSTRACT

A speculum, comprising a handle portion including a proximal end, a distal end and at least one sidewall connecting the proximal end and the distal end and having a cavity in the sidewall thereof, a lower blade connected to the handle portion, an upper blade movably connected to the lower blade, the upper and lower blades being configured to move relative to one another between a closed state and an open state, and a lighting assembly comprising at least one light source and at least one energy storage device, said lighting assembly being at least partially disposed in the cavity in the sidewall of the handle portion.

33 Claims, 17 Drawing Sheets

Related U.S. Application Data

Jun. 26, 2014, now Pat. No. 9,913,577, which is a continuation-in-part of application No. 13/241,136, filed on Sep. 22, 2011, now Pat. No. 9,307,897.

(60) Provisional application No. 61/387,038, filed on Sep. 28, 2010.

(51) Int. Cl.
*A61B 1/07* (2006.01)
*A61B 1/32* (2006.01)

(56) References Cited

U.S. PATENT DOCUMENTS

| | | |
|---|---|---|
| 3,332,414 A | 7/1967 | Gasper |
| 3,532,088 A | 10/1970 | Fiore |
| 3,592,199 A | 7/1971 | Ostensen |
| 3,595,222 A | 7/1971 | Vellacott |
| 3,675,641 A | 7/1972 | Fiore |
| 3,762,400 A | 10/1973 | McDonald |
| 3,789,835 A | 2/1974 | Whitman |
| 3,815,585 A | 6/1974 | Fiore |
| 3,934,578 A | 1/1976 | Heine |
| 3,945,371 A | 3/1976 | Adelman |
| 3,978,850 A | 9/1976 | Moore et al. |
| 4,067,323 A | 1/1978 | Troutner |
| 4,156,424 A | 5/1979 | Burgin |
| 4,210,133 A | 7/1980 | Castaneda |
| 4,263,899 A | 4/1981 | Burgin |
| 4,300,541 A | 11/1981 | Burgin |
| 4,337,763 A | 7/1982 | Petrassevich |
| 4,432,351 A | 2/1984 | Hoary |
| 4,492,220 A | 1/1985 | Hayes |
| 4,502,468 A | 3/1985 | Burgin |
| 4,546,761 A | 10/1985 | McCulough |
| 4,562,832 A | 1/1986 | Wilder |
| 4,566,439 A | 1/1986 | Burgin |
| 4,597,383 A | 7/1986 | Bel |
| 4,607,623 A | 8/1986 | Bauman |
| 4,619,248 A | 10/1986 | Walsh |
| 4,638,792 A | 1/1987 | Burgin |
| 4,766,887 A | 8/1988 | Cecil, Jr. et al. |
| 4,807,600 A | 2/1989 | Hayes |
| 4,884,559 A | 12/1989 | Collins |
| 4,934,352 A | 6/1990 | Sullivan, Jr. |
| 4,971,036 A | 11/1990 | Collins |
| 5,018,507 A | 5/1991 | Montaldi |
| 5,026,368 A | 6/1991 | Adair |
| 5,054,906 A | 10/1991 | Lyons |
| 5,063,908 A | 11/1991 | Collins |
| 5,143,054 A | 9/1992 | Adair |
| 5,165,387 A | 11/1992 | Woodson |
| 5,174,278 A | 12/1992 | Babkow |
| 5,179,937 A | 1/1993 | Lee |
| 5,222,271 A | 6/1993 | Eganhouse |
| 5,329,938 A | 7/1994 | Lonky |
| 5,427,152 A | 6/1995 | Weber |
| 5,465,709 A | 11/1995 | Dickie et al. |
| 5,499,964 A * | 3/1996 | Beck ............ A61B 1/0669 600/223 |
| 5,553,627 A | 9/1996 | Newkirk |
| 5,695,492 A | 12/1997 | Brown |
| 5,716,329 A | 2/1998 | Dieter |
| 5,785,648 A | 7/1998 | Min |
| 5,846,249 A | 12/1998 | Thompson |
| 5,865,729 A | 2/1999 | Meehan |
| 5,873,820 A | 2/1999 | Norell |
| 5,899,854 A | 5/1999 | Slishman |
| 5,916,150 A | 6/1999 | Sillman |
| 6,004,265 A | 12/1999 | Hsu et al. |
| 6,036,638 A | 3/2000 | Nwawka |
| 6,036,713 A | 3/2000 | Kieturakis |
| 6,048,308 A | 4/2000 | Strong |
| 6,176,824 B1 | 1/2001 | Davis |
| 6,186,944 B1 | 2/2001 | Tsai |
| 6,217,512 B1 | 4/2001 | Salo et al. |
| 6,231,505 B1 | 5/2001 | Martin |
| 6,254,247 B1 | 7/2001 | Carson |
| 6,277,067 B1 | 8/2001 | Blair |
| 6,280,379 B1 * | 8/2001 | Resnick ............ A61B 1/32 600/220 |
| 6,319,199 B1 | 11/2001 | Sheehan et al. |
| 6,346,085 B1 | 2/2002 | Schiffman |
| 6,359,644 B1 | 3/2002 | Salvati |
| 6,361,489 B1 | 3/2002 | Tsai |
| 6,379,296 B1 * | 4/2002 | Baggett ............ A61B 1/303 600/179 |
| 6,379,299 B1 | 4/2002 | Borodulin et al. |
| 6,394,111 B1 | 5/2002 | Jacobs et al. |
| 6,394,950 B1 | 5/2002 | Weiss |
| 6,432,045 B2 | 8/2002 | Lemperle |
| 6,432,049 B1 | 8/2002 | Banta |
| 6,436,033 B2 | 8/2002 | Tan |
| 6,450,952 B1 | 9/2002 | Rioux |
| 6,468,206 B1 | 10/2002 | Hipps et al. |
| 6,468,232 B1 | 10/2002 | Ashton-Miller et al. |
| 6,487,440 B2 | 11/2002 | Deckert et al. |
| 6,524,259 B2 | 2/2003 | Baxter-Jones et al. |
| 6,569,091 B2 | 5/2003 | Diokno et al. |
| 6,589,168 B2 | 7/2003 | Thompson |
| 6,595,917 B2 | 7/2003 | Nieto |
| 6,626,825 B2 | 9/2003 | Tsai |
| 6,663,576 B2 | 12/2003 | Gombrich et al. |
| 6,761,687 B1 | 7/2004 | Doshi |
| 6,830,547 B2 | 12/2004 | Weiss |
| 6,896,653 B1 | 5/2005 | Vail, III et al. |
| 7,014,340 B2 | 3/2006 | Betis |
| 7,029,439 B2 | 4/2006 | Roberts et al. |
| D520,464 S | 5/2006 | Strong |
| 7,276,025 B2 | 10/2007 | Roberts et al. |
| 7,631,981 B2 | 12/2009 | Miller et al. |
| 7,878,973 B2 | 2/2011 | Yee et al. |
| 8,052,702 B2 | 11/2011 | Hess et al. |
| 8,096,945 B2 | 1/2012 | Buchok et al. |
| 8,292,805 B2 | 10/2012 | Vayser et al. |
| 8,795,162 B2 | 8/2014 | Vayser et al. |
| 8,870,761 B2 | 10/2014 | Vayser et al. |
| 9,044,161 B2 | 6/2015 | Vayser et al. |
| 9,072,452 B2 | 7/2015 | Vayser et al. |
| 9,241,617 B2 | 1/2016 | Grey et al. |
| 9,271,709 B2 | 3/2016 | Grey et al. |
| 9,271,710 B2 | 3/2016 | Grey et al. |
| 9,282,878 B2 | 3/2016 | Grey et al. |
| D753,295 S | 4/2016 | Vivenzio et al. |
| 9,308,054 B2 | 4/2016 | Vayser et al. |
| 9,468,366 B2 | 10/2016 | Grey et al. |
| 9,510,737 B2 | 12/2016 | Vayser et al. |
| 9,532,706 B2 | 1/2017 | McMahon et al. |
| 9,629,529 B1 | 4/2017 | Indovina et al. |
| 9,636,182 B2 | 5/2017 | Vayser et al. |
| 9,833,295 B2 | 12/2017 | Vayser et al. |
| 10,092,176 B2 | 10/2018 | Kienzle et al. |
| 10,092,281 B2 | 10/2018 | Perler et al. |
| 10,098,530 B2 | 10/2018 | McMahon et al. |
| 10,105,043 B2 | 10/2018 | George |
| 10,117,646 B2 | 11/2018 | Friedrich et al. |
| 10,130,441 B2 | 11/2018 | Martinez |
| 10,342,525 B2 | 7/2019 | Wilson |
| 2002/0115909 A1 | 8/2002 | Bolser |
| 2003/0105387 A1 | 6/2003 | Frumovitz et al. |
| 2005/0085723 A1 | 4/2005 | Huebner |
| 2005/0125015 A1 | 6/2005 | McNally-Heintzelman et al. |
| 2005/0277811 A1 | 12/2005 | Richards et al. |
| 2006/0189847 A1 | 8/2006 | Yee et al. |
| 2006/0200186 A1 | 9/2006 | Marchek et al. |
| 2007/0043264 A1 | 2/2007 | Gillis et al. |
| 2007/0060938 A1 | 3/2007 | Dziadik et al. |
| 2007/0230164 A1 | 10/2007 | Vivenzio et al. |
| 2007/0230167 A1 | 10/2007 | McMahon et al. |
| 2007/0255110 A1 * | 11/2007 | Wax ............ A61B 1/303 600/223 |
| 2007/0270866 A1 | 11/2007 | Von Jako |
| 2007/0287888 A1 | 12/2007 | Lovell et al. |

(56) References Cited

U.S. PATENT DOCUMENTS

| | | | |
|---|---|---|---|
| 2008/0221569 A1 | 9/2008 | Moore et al. | |
| 2008/0228038 A1* | 9/2008 | McMahon | A61B 1/00114 |
| | | | 600/223 |
| 2008/0269565 A1* | 10/2008 | McMahon | A61B 1/303 |
| | | | 600/245 |
| 2008/0278936 A1 | 11/2008 | Kurth et al. | |
| 2009/0097236 A1* | 4/2009 | Miller | A61B 90/30 |
| | | | 362/119 |
| 2009/0275803 A1 | 11/2009 | Krauter et al. | |
| 2009/0287192 A1 | 11/2009 | Vivenzio et al. | |
| 2009/0312610 A1* | 12/2009 | Buchok | A61B 1/00137 |
| | | | 600/223 |
| 2010/0041955 A1* | 2/2010 | Grey | A61L 29/041 |
| | | | 600/212 |
| 2010/0292533 A1 | 11/2010 | Kasahara et al. | |
| 2011/0275894 A1 | 11/2011 | Mackin | |
| 2013/0102887 A1 | 4/2013 | Thompson et al. | |
| 2013/0158345 A1 | 6/2013 | Majlessi | |
| 2013/0197313 A1 | 8/2013 | Wan | |
| 2013/0245657 A1 | 9/2013 | Deville et al. | |
| 2014/0088371 A1 | 3/2014 | Vayser et al. | |
| 2014/0257039 A1 | 9/2014 | Feldman | |
| 2014/0316211 A1 | 10/2014 | Hermle | |
| 2014/0323800 A1 | 10/2014 | Dye | |
| 2014/0364695 A1 | 12/2014 | Nadershahi et al. | |
| 2015/0238070 A1 | 8/2015 | Lia et al. | |
| 2015/0285382 A1 | 10/2015 | Kienreich et al. | |
| 2016/0030128 A1 | 2/2016 | Duggal et al. | |
| 2016/0066915 A1 | 3/2016 | Baber et al. | |
| 2016/0302657 A1 | 10/2016 | Hussey et al. | |
| 2017/0065282 A1 | 3/2017 | Mathis et al. | |
| 2017/0224206 A1 | 8/2017 | Vayser | |
| 2017/0231712 A1 | 8/2017 | Vayser | |
| 2018/0014842 A1 | 1/2018 | Shener-Irmakoglu | |
| 2018/0271581 A1 | 9/2018 | Ouyang et al. | |
| 2018/0280011 A1 | 10/2018 | Ferro et al. | |
| 2018/0296082 A1 | 10/2018 | Salvati et al. | |
| 2018/0317746 A1 | 11/2018 | Lalli et al. | |
| 2018/0317752 A1 | 11/2018 | Cybulski et al. | |
| 2018/0317902 A1 | 11/2018 | Green et al. | |
| 2018/0328572 A1 | 11/2018 | Kennedy et al. | |
| 2019/0254512 A1 | 8/2019 | Spiertz | |
| 2019/0335988 A1 | 11/2019 | Lia et al. | |
| 2019/0343379 A1 | 11/2019 | Altamura | |
| 2019/0365217 A1 | 12/2019 | Hegenberger | |
| 2020/0008694 A1 | 1/2020 | Karla et al. | |
| 2020/0046216 A1 | 2/2020 | Moein | |
| 2020/0069171 A1 | 3/2020 | Miller et al. | |

FOREIGN PATENT DOCUMENTS

| | | |
|---|---|---|
| DE | 202004002963 | 5/2004 |
| DE | 202005019780 | 5/2006 |
| DE | 202010017638 | 5/2012 |
| GB | 2505463 | 5/2014 |
| RU | 2187972 | 8/2002 |
| WO | WO 2013-044151 | 3/2013 |
| WO | WO 2014041172 | 3/2014 |
| WO | WO 2016196788 | 12/2016 |

OTHER PUBLICATIONS

OBP Medical—ER-Spec Brochure published Apr. 11, 2013 (2 pages).
OBP Medical—ER-Spec Brochure published Feb. 4, 2013 (2 pages).
OBP Medical—ER-Spec Brochure, Light Source Now 10X Brighter published Jan. 23, 2013 (1 page).
OBP Medical—ER-Spec Brochure, Light Source Now 10X Brighter published Oct. 30, 2012 (1 page).
OBP Medical—ER-Spec Obgyn Brochure published Nov. 19, 2014 (2 pages).
OBP Medical—ER-Spec Product Presentation published Apr. 16, 2014 (12 pages).
OBP Medical—OfficeSPEC, Premier Speculum for In-Office Procedures published Nov. 30, 2009 (1 page).
Pankaj Saxena, et al., Hydrodissection Technique of Harvesting Left Internal Thoracic Artery, Department of Cardiac Surgery, The Prince Charles Hospital, Chermside, Brisbane, Queensland, Australia, Thoracic Artery, Ann Thorac Burg., 2005; 80:335-6.
Redefining illumination, Eikon LT Adapt SE For optimal precision and protection (2019), St,yker, www.stlyker.com/surgical (3 pages).
The above documents were cited in a European Search Report issued on Nov. 23, 2018, that issued in the corresponding European Patent Application No. 16747107.7.
The above patent was cited in a Oct. 29, 2018 Chinese Office Action, a copy of which is enclosed without an English Translation, that issued in Chinese Patent Application No. 201711159829.6.
Whe above U.S. Publications documents #1 and #2 were cited in a Supplementary European Search Report issued on Apr. 24, 2019, that issued in European Patent Application No. 16804432.9.

\* cited by examiner

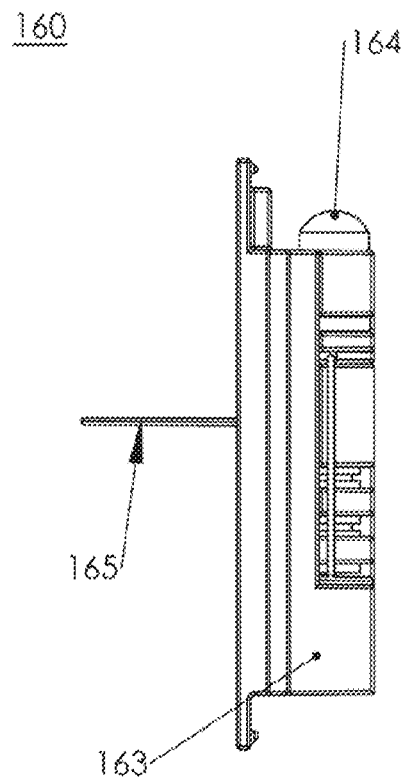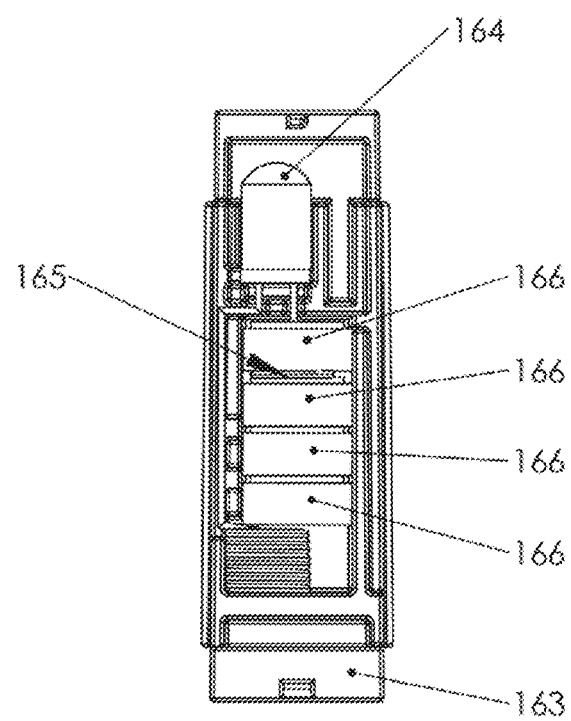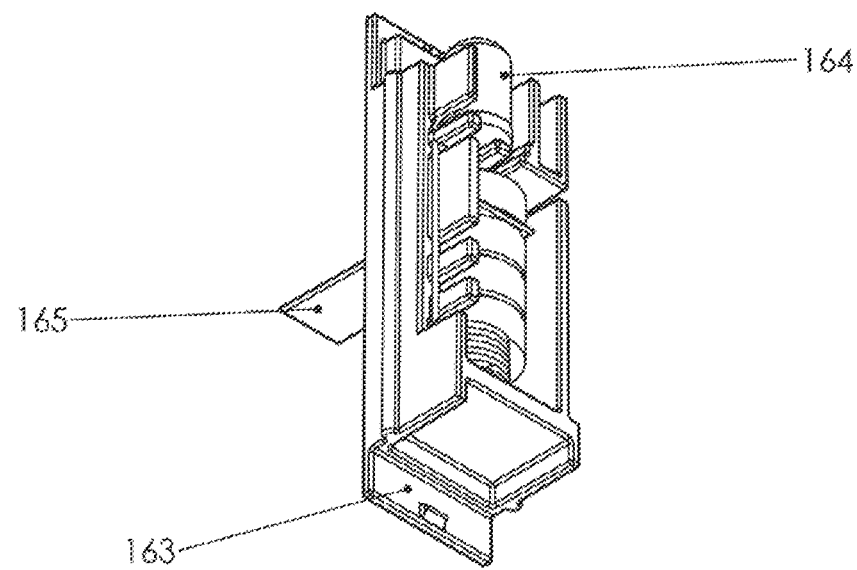
FIG. 10C
FIG. 10B
FIG. 10A

SPECULUM

RELATED APPLICATIONS

This application is a divisional of U.S. application Ser. No. 16/515,371, filed Jul. 18, 2019, which is a continuation of U.S. application Ser. No. 14/748,435, filed Jun. 24, 2015, now U.S. Pat. No. 10,368,733, which is a continuation of U.S. application Ser. No. 14/316,787, filed Jun. 26, 2014, now U.S. Pat. No. 9,913,577, which is a continuation-in-part of U.S. application Ser. No. 13/241,136 filed Sep. 22, 2011, entitled "DISPOSABLE SPECULUM HAVING LATERAL STABILIZING MECHANISM," now U.S. Pat. No. 9,307,897, which claims the benefit of Provisional Application No. 61/387,038 filed Sep. 28, 2010. All of these applications are incorporated herein by reference in their entireties.

BACKGROUND

Technical Field

The present disclosure relates to speculums.

Description of Related Art

A speculum is a medical instrument for dilating the opening of a body cavity for medical examination. A vaginal speculum commonly used during a gynecological examination or a surgical procedure is introduced into a patient's vagina to separate the vaginal walls, thus allowing the internal genital organs to be examined. Metal, autoclavable duck-bill specula are conventionally used for gynecological examination and treatment. These units, with exposed joints, sharp edges, and cold metal are universally disliked by patients. The hinged joints and blade edges often pinch, scrape, or otherwise traumatize the supporting tissues in the area being examined. The conventional metallic specula blades are typically opaque. Therefore, the only area available for inspection when a metallic speculum is in use is the open end, for cervical examination, and the vaginal wall areas between the blades.

In an attempt to eliminate some of the problems mentioned above, plastic specula have been developed. Plastic specula, which are formed from plastic or another lightweight and inexpensive material, are often designed with a double-hinge. Although these double-hinge designs satisfactorily support the vertical stresses placed on the speculum, current designs allow for significant movement when exposed to lateral forces. Such lateral forces are common when vaginal muscles become tense during procedures which do not require anesthesia, and the resulting lateral movement is objectional to the physician because it can result in speculum movement inside the vagina, or in the worst case speculum collapse.

Sufficient lighting of the subject area for examination is another area of difficulty, since typical specula are not equipped with illumination devices. Light must be directed from another source, often a gooseneck lamp that can partially obstruct the view into the vagina. Head-mounted lights have been used as a partial solution to this problem, but such head-mounted lights are uncomfortable for the operator and cumbersome due to the light cord. Lights built into the handle of existing specula generally project into a light pipe which follows up the center of the speculum. Since this light and light pipe assembly occupy the center of the handle the speculum hinge mechanism must be offset to one side. However, such offsetting from the center of the speculum has the undesirable effect of increasing lateral movement resulting from stress.

SUMMARY

According to one embodiment of the present disclosure, a speculum includes an upper blade, a lower blade, a link member, a handle portion, a curved portion, and a light source. The link member connects the upper blade and the lower blade to allow the upper blade and the lower blade to move between an open state and a close state. The curved portion connects the lower blade and the handle portion. The light source is disposed on the curved portion.

According to another embodiment of the present disclosure, a speculum includes an upper blade, a lower blade, a link member, a handle portion, and a light source. The link member connects the upper blade and the lower blade to allow the upper blade and the lower blade to move between an open state and a close state. The handle portion is connected to the lower blade. The light source is disposed on the junction of the lower blade and the handle portion.

BRIEF DESCRIPTION OF THE DRAWINGS

FIG. 1A is a perspective view of the vaginal speculum.

FIG. 1B is a rear view of the vaginal speculum.

FIG. 4A is a rear perspective view of the lower member. FIG. 4B is a front perspective view of the lower member.

FIG. 8A is a side view of the upper member secured to the linear support member. FIG. 8B is a perspective view of the upper member secured to the linear support member.

FIG. 10A, FIG. 10B and FIG. 100 show an embodiment of a light source for use with the vaginal speculum of FIG. 1A and FIG. 1B. FIG. 10A is a perspective view of the light source showing some of the outer and the inner components. FIG. 10B is a back view of the light source showing inner components. FIG. 10C is a side view of the light source showing some of the outer components.

Figure 1A:
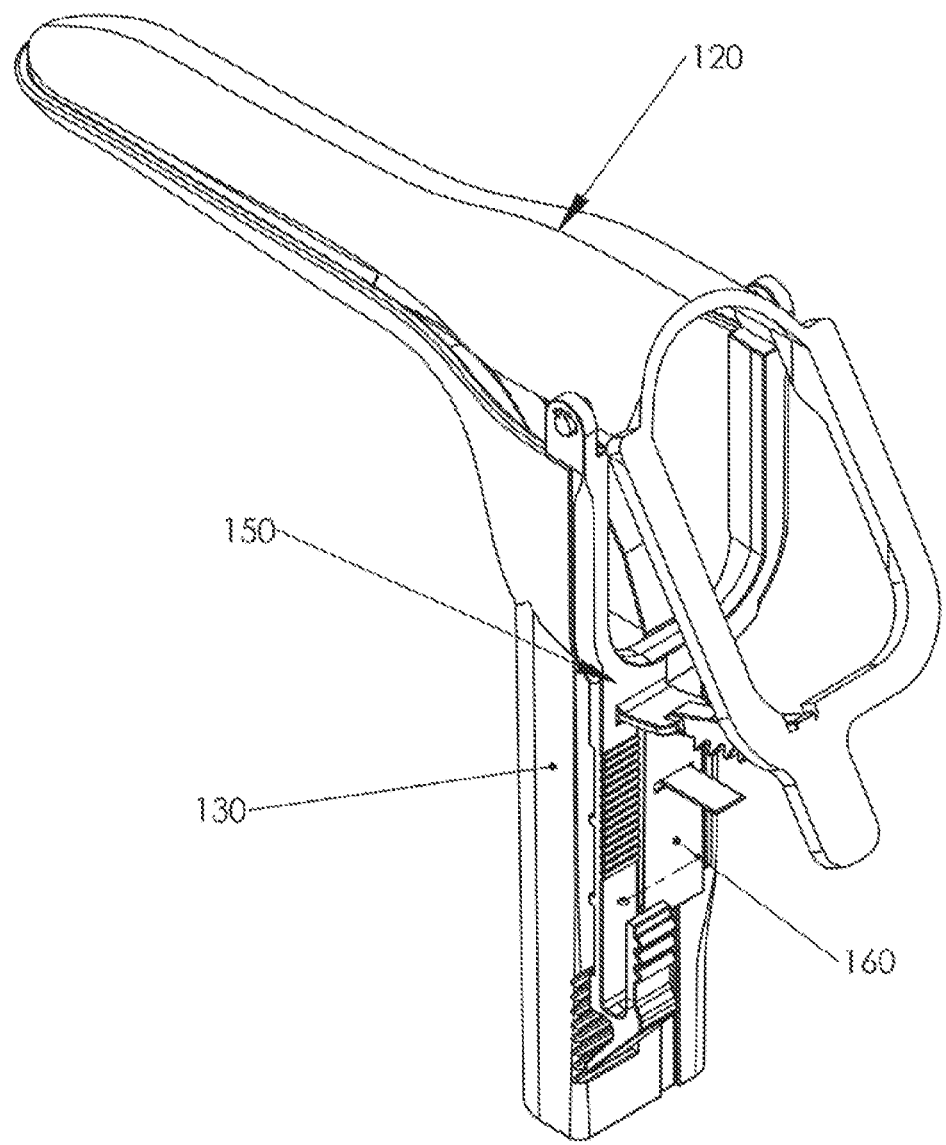
FIG. 1A and FIG. 1B show an embodiment of a vaginal speculum of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Vaginal speculums having lateral stabilized support and operating mechanisms are disclosed herein. The disclosed vaginal speculums are fabricated from plastic materials, and are designed to be for single-use and are fully disposable. Although the vaginal speculums disclosed herein are intended to be used by gynecologists, it is understood that the vaginal speculums may also be used for example, by primary care physicians, geriatricians, urologists and nurse practitioners.

As used herein, the term "cross-contamination" refers to the passing of bacteria or viruses indirectly from one patient to another through the use of improper sterilization procedures, unclean instruments, or recycling of products.

As used herein, the term "disposable" refers to a vaginal speculum of the present disclosure designed for short-term convenience, and intended for single-use. The disposable vaginal speculum therefore does not need to be sterilized after use, which reduces the cost of maintaining the vaginal speculum, and minimizes the risk of cross-contamination.

As used herein, the term "female internal genital organs" refers to the vulva, vagina and cervix.

As used herein, the term "gynecological examination" or "surgical procedure" refers to a medical procedure performed on a female patient to visualize, inspect, and/or remove a portion of the female internal genital organs. Common gynecological procedures and surgeries include, but are not limited to, colposcopy, cervical cryosurgery, loop electrosurgical excision procedure (LEEP) procedure, hysteroscopy, dilation and curettage (D&C), cervical biopsy, transcervical chorionic villus sampling, endometrial ablation, endometrial biopsy, vaginal hysterectomy and PAP test.

The vaginal speculums disclosed herein can be used during various medical procedures, and more particularly are used for gynecological procedures either in an office or a hospital setting.

As used herein, the term "elevational movement" refers to the vertical up-and-down movement of an upper blade relative to a lower blade of a vaginal speculum of the present disclosure.

As used herein, the term "linear" refers to a straight line of material, for example, a straight line of plastic material. A linear support member refers to a support member of the present disclosure that is made from a straight line of plastic material, having no curves or angles.

As used herein, the term "angulational movement" refers to the angular up-and-down movement of an upper blade relative to a lower blade of a vaginal speculum of the present disclosure.

As used herein, the term "lateral movement" refers to the sideways back and forth movement of an upper blade relative to a lower blade of a vaginal speculum of the present disclosure.

As used herein, the term "open state" refers to the positioning of an upper blade and a lower blade of a vaginal speculum of the present disclosure at a spaced-apart distance. The open state may be accomplished by elevating a support member that connects the upper blade and the lower blade together, by angularly moving the upper blade relative to the lower blade, or by a combination of both.

As used herein, the term "working space" refers to a space created between an upper blade and a lower blade of a speculum of the present disclosure. In an embodiment, the working space is created for viewing, examining, and performing surgical procedures on female internal genital organs.

As used herein, the term "structural integrity" refers to a feature provided by a vaginal speculum of the present disclosure prior to, during, and after use. An upper blade and a lower blade of the speculum are designed to withstand applied loads and transfer these applied loads to various other components of the speculum, while maintaining the structural integrity of the speculum.

As used herein, the term "fulcrum" refers to a support structure created by engaging a support member and a support structure of a vaginal speculum of the present disclosure. The created fulcrum results in the ability for an upper blade of the vaginal speculum to angularly move with relation to a lower blade of the vaginal speculum.

Figure 1B:
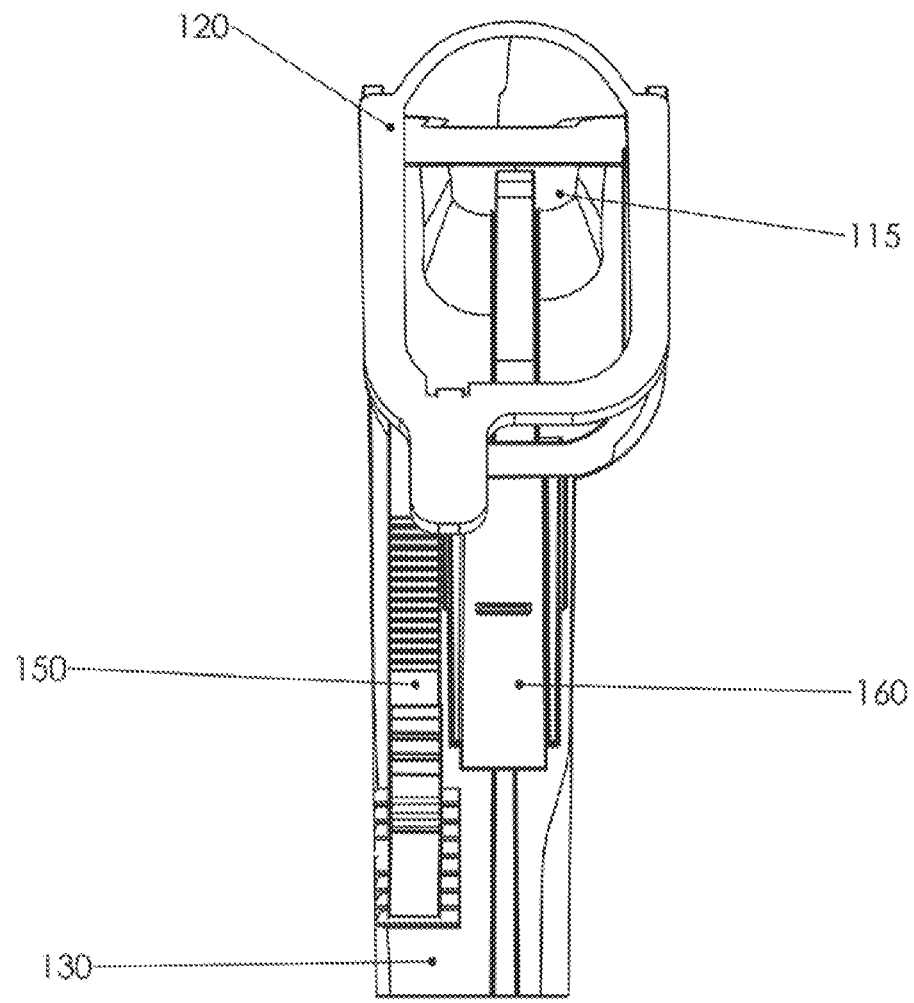

As shown in FIG. 1A and FIG. 1B, a disposable vaginal speculum 100 of the present disclosure includes an upper member 120, a linear support member 150, and a lower member 130 having a built-in light source 160. The linear support member 150 is engaged to both the upper member 120 and the lower member 130, as will be described in detail below. Unlike metallic speculums, which are not designed for single-use but instead are meant to be re-used many times with sterilization occurring between each use, the entire speculum 100 of the presently disclosed embodiments is fabricated from one or more plastics or plastic composites, sterilized when manufactured or packaged, and sufficiently inexpensive to be discarded after only one use. Sterilization of reusable specula can be costly and time-consuming. More significantly, if sterilization is not done properly, blood borne pathogens or other harmful biological agents from one patient can survive the sterilization process and be transmitted to another patient. Because the entire speculum 100 of the presently disclosed embodiments is disposable, there is no need to sterilize the speculum 100 after each use, which greatly reduces the time and cost associated with such sterilization procedures and prevents cross-contamination. Exemplary plastic materials which may be used to construct the various components of the speculum 100 include, but are not limited to, polypropylene, polyester, polyethylene, acrylic, polycarbonate, polyamide, polystyrene, and any composite of more than one of these plastics.

In an embodiment, the upper member 120 and the lower member 130 are fabricated from plastic materials that are substantially rigid and capable of transmitting light. For example, the upper member 120 and the lower member 130 may be molded from a colorless transparent plastic material such as acrylic plastic or the like. Acrylic plastic is relatively rigid, can be injection molded or extruded, and has excellent light conductive properties most suitable for use with the speculum 100 of the present disclosure. In an embodiment, the linear support member 150 is fabricated from a different plastic material than the upper member 120 and the lower member 130. The linear support member 150 is fabricated from a rigid, sturdy, plastic material that can handle various load patterns, as will be described in detail below. In an embodiment, the upper member 120 and the lower member 130 are fabricated from a polycarbonate material. In an embodiment, the linear support member 150 is fabricated from a polyester material. In an embodiment, the linear support member 150 is fabricated from a polyamide material, for example, nylon.

Figure 2:
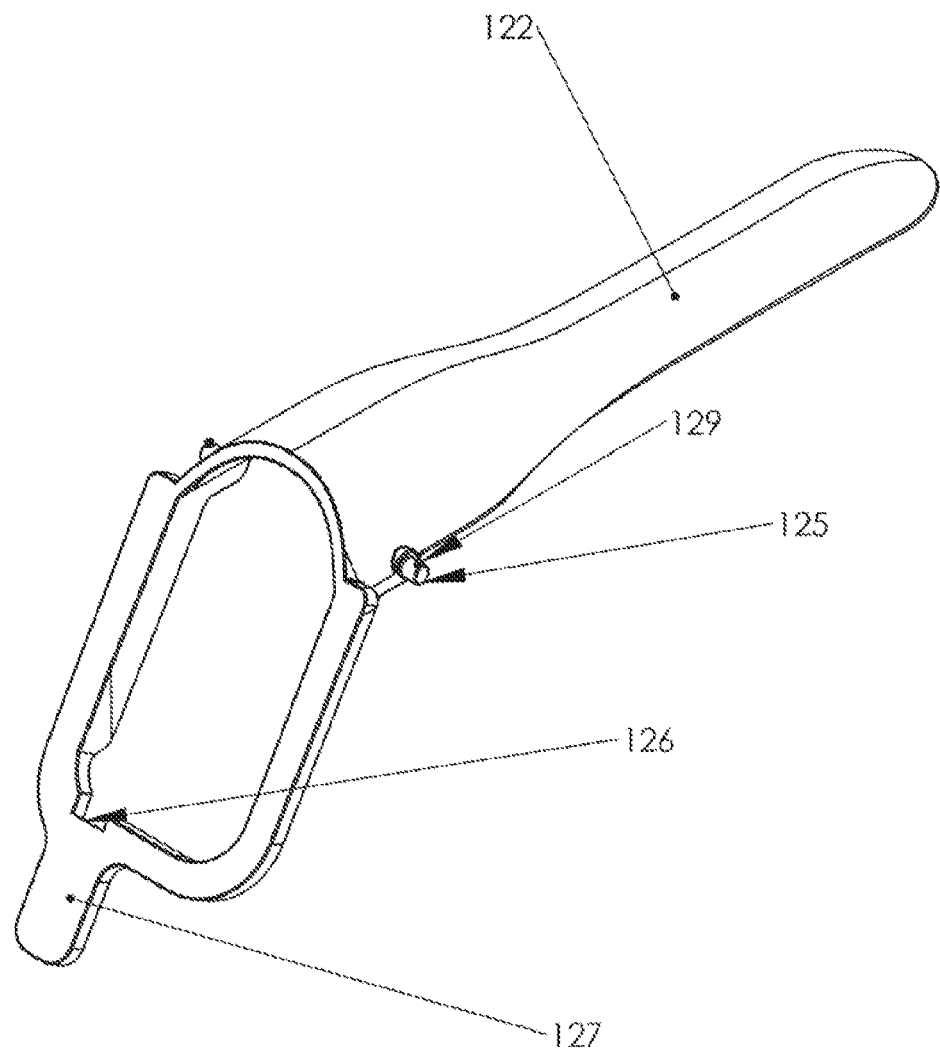
FIG. 2 is a perspective view of an upper member of the vaginal speculum of FIG. 1A.

As best illustrated in FIG. 2, the disposable speculum 100 comprises an upper member 120 having an upper blade 122 that terminates in a hinge assembly 125. The hinge assembly 125 receives and transfers loads placed on the upper member 120 and the lower member 130 to various components of the speculum 100, as will be described in detail below. The hinge assembly 125 includes an operating mechanism 127 which extends out from the hinge assembly 125. As shown in the embodiments depicted in the figures, the operating mechanism 127 is located on a left-side of the upper blade 122. In another embodiment, the operating mechanism 127 may be located on a right-side of the upper blade 122. The unique design and low profile of the hinge assembly 125 enable a user of the speculum 100 to have a large unobstructed view of a patient during a gynecological procedure. In an embodiment, the operating mechanism 127 extends out and down from the upper blade 122 at an angle. Also, a working space 115 created when the speculum 100 is in an open state (see FIG. 1B, the speculum 100 is not shown entirely in the open state in the figures) provides exceptional instrument maneuverability to the user of the speculum 100. The speculums known in the art often provide a limited working space with limited visibility due to a poorly designed hinge assembly.

Figure 3:
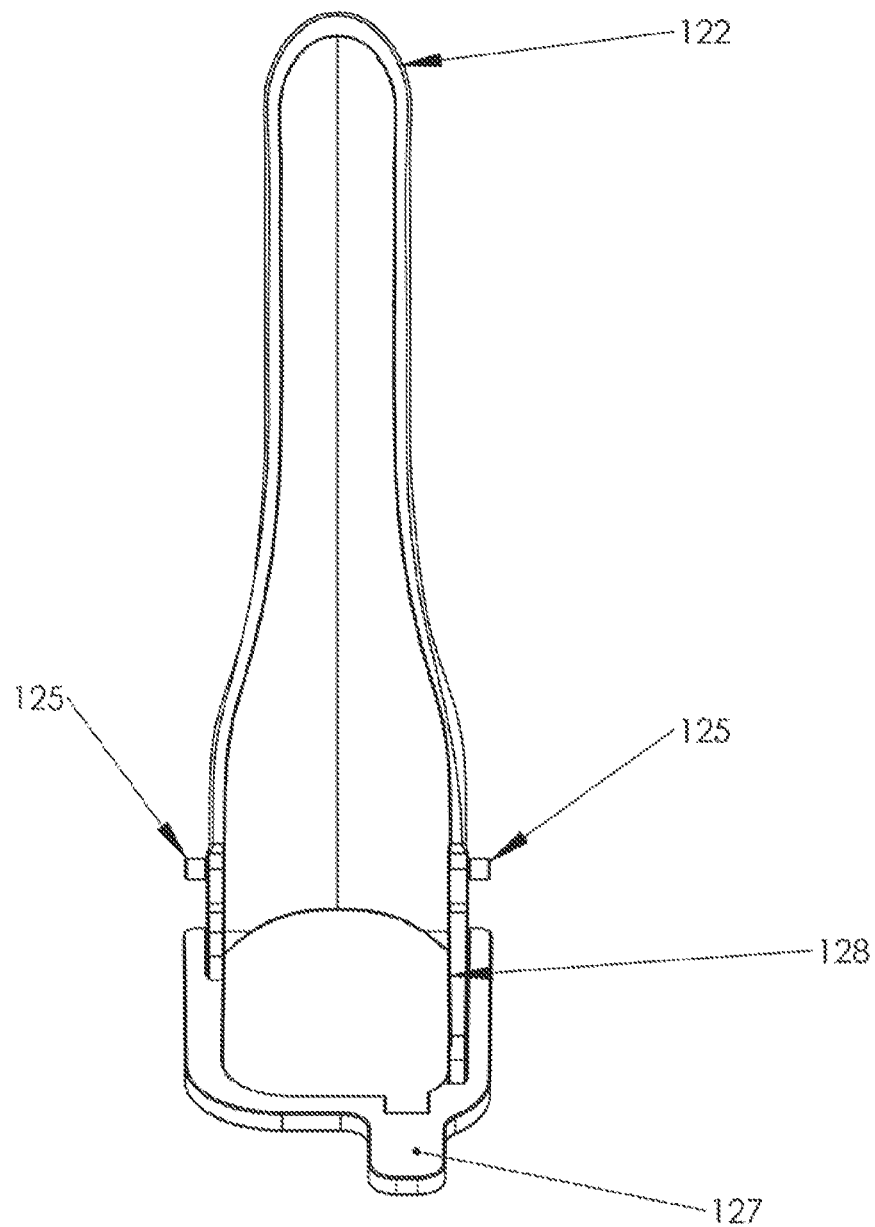
FIG. 3 is a plan view showing an interior side of the upper member of the vaginal speculum of FIG. 2. The upper member includes an upper blade, a supporting structure, and an operating mechanism.

As shown in FIG. 2 and FIG. 3, the hinge assembly 125 comprises a pair of parallel support beams 129 spaced a distance apart. These parallel support beams 129 will interact with the support member 150 to prevent hinge slippage when a lateral force is present. The operating mechanism 127 interacts with an angulation arm 157 on the support member 150 which allows a user of the speculum 100 to move the upper blade 122 at various angles when pressure is applied to the operating mechanism 127 during use of the speculum 100. The operating mechanism 127 is formed with an opening 126 for which the angulation arm 157 of the linear support member 150 moves through and locks with. The upper blade 122 has a thickness, a width and a curve, which prevents failure of the upper blade 122 with the application of pressure or stress, for example during a gynecological procedure. In an embodiment, the upper blade 122 has a rounded distal end.

Figure 4A:
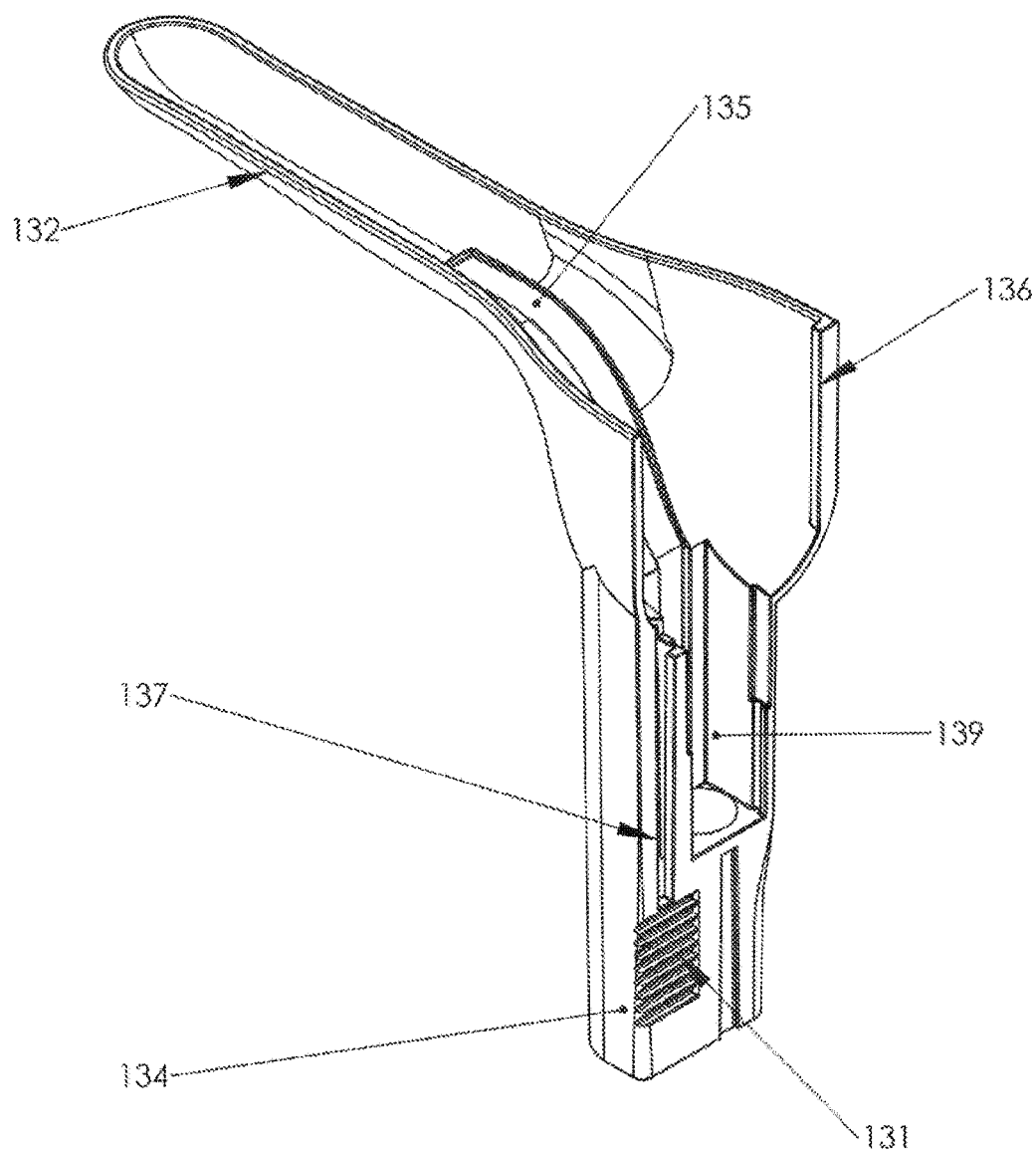
FIG. 4A and FIG. 4B are perspective views of a lower member of the vaginal speculum of FIG. 1A.
Figure 4B:
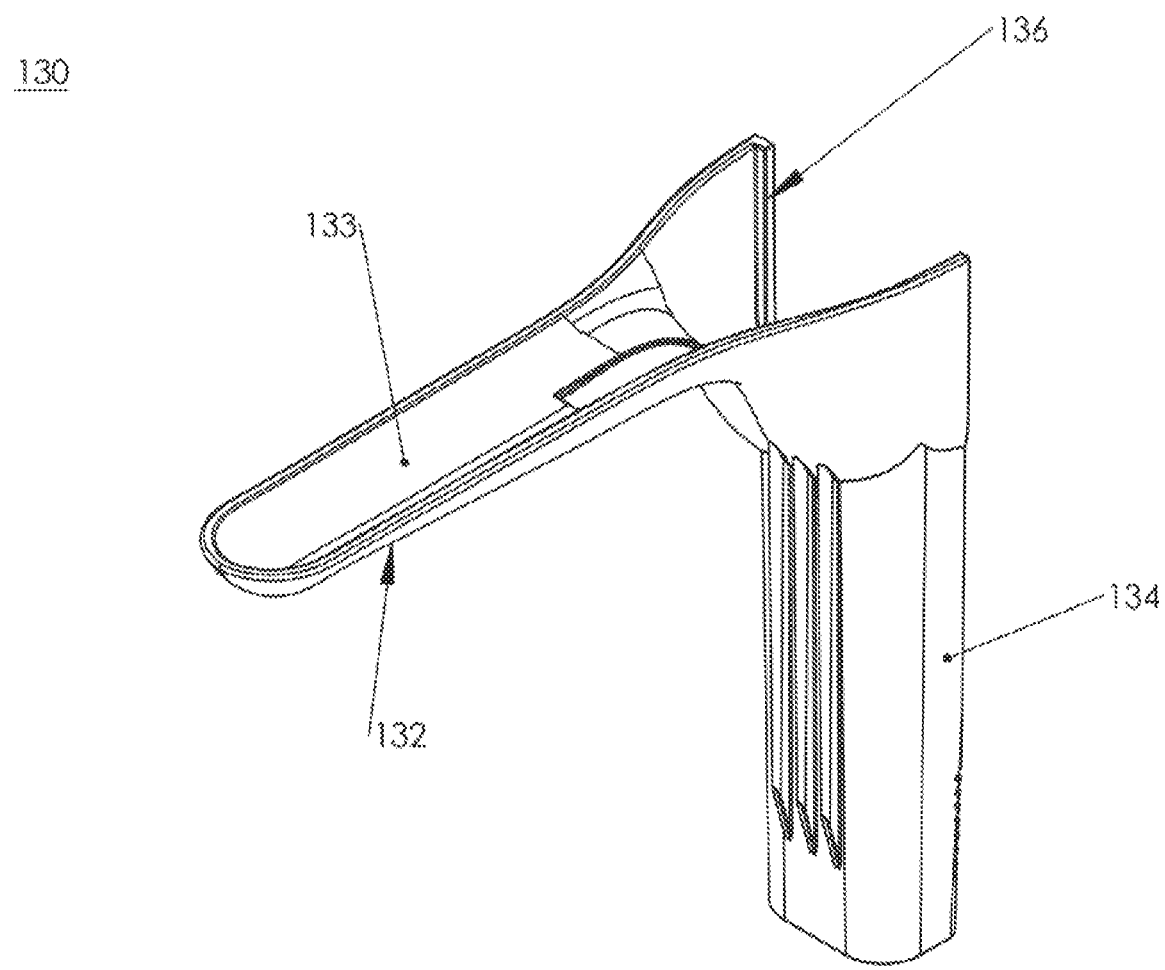

FIG. 4A and FIG. 4B show the lower member 130 of the speculum 100. The lower member 130 includes a lower blade 132 and a handle portion 134. The handle portion 134 includes a vertical track 137 for elevational movement of the linear support member 150, and a cavity 139 for positioning of the built-in light source 160 (see FIG. 1A or FIG. 1B). In an embodiment, the track 137 is a carved-out space positioned at a single side of the handle portion 134. On an outer surface of the handle 134 at a distal end of the track 137, there are stop tabs 131. These stop tabs 131 encounter a locking tooth 159 on an elevation leg 155 of the linear support member 150 (see FIG. 7) and maintain the speculum 100 in an open state at various, user-selected distances. Because the light source cavity 139 is typically placed in the center of handle 134, the track 137 for support member 150 is ideally placed either to the left or the right of the light source cavity 139. Such placement of the support track 137 will cause translation of the normal vertical stress placed upon top member 120 into a lateral force. A typical speculum will suffer lateral movement of the top blade as a result. This lateral movement interferes with many physician procedures, can cause patient discomfort, and may lead to a structural failure of the speculum. To eliminate this lateral movement a novel support structure 136 has been added so as to protrude slightly into the viewing area 115. This support structure 136 interacts with a hidden slot 191 in support member 150 (see FIG. 7) to substantially eliminate lateral movement. The support structure 136 is shown on the right side of the lower member 130. In an embodiment, the support structure 136 and the hidden slot 191 are located on the right side of the speculum 100. In another embodiment, the support structure 136 and the hidden slot 191 are located on both sides of speculum 100.

As shown in the embodiment depicted in FIG. 4B, the handle 134 has at least one shaped surface so that a user of the speculum 100 may easily grasp the handle 134. The lower blade 132 has a thickness, a width, and a curve which prevents failure of the blade 132 with the application of pressure or stress. In an embodiment, the lower blade 132 has a rounded distal end.

Figure 5:
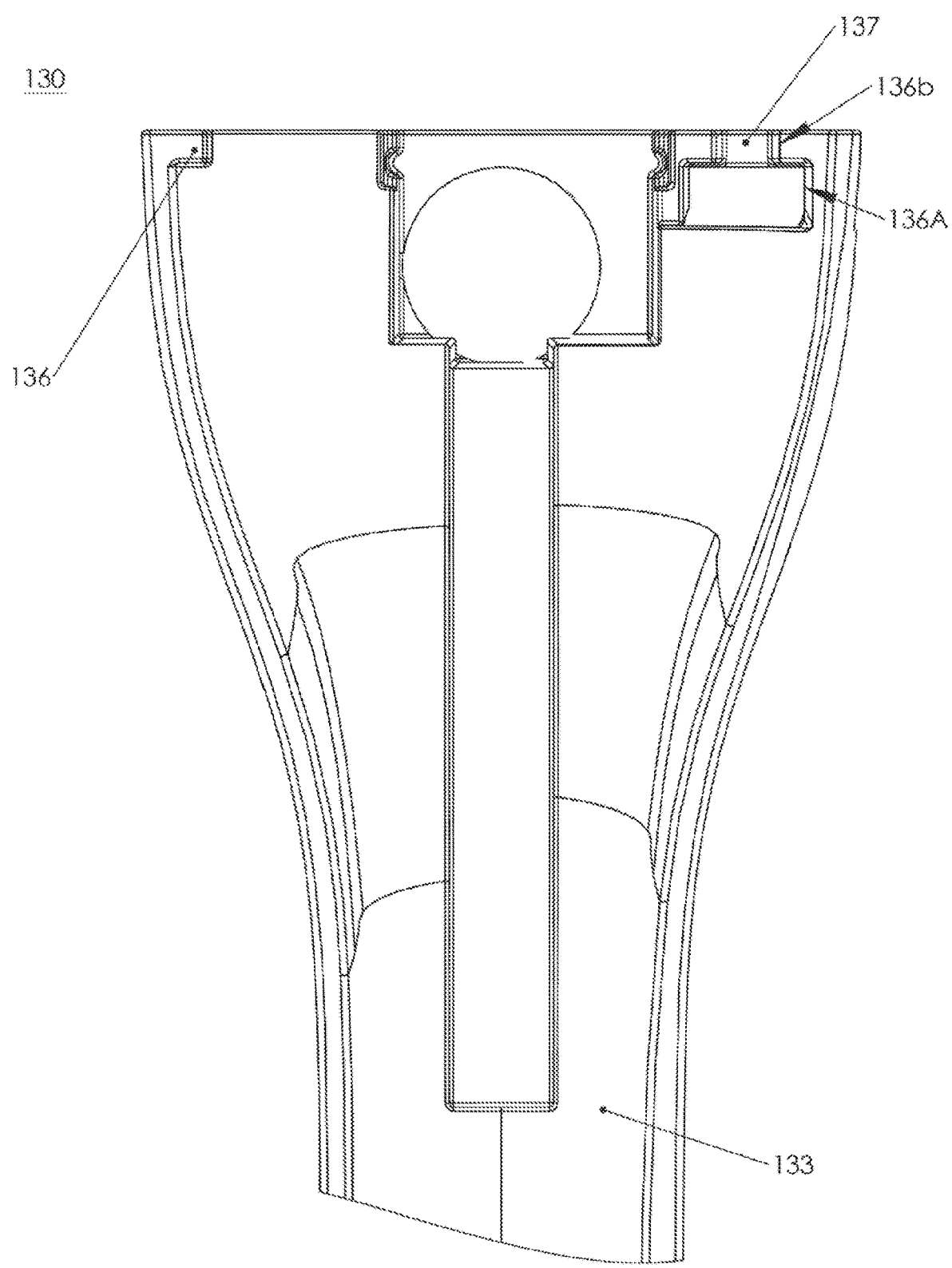
FIG. 5 is a close-up plan view of the lower member of the vaginal speculum of FIG. 4A and FIG. 4B. The lower member includes a lower blade and a track for engaging a linear support member.

FIG. 5 shows a close-up plan view showing an interior surface 133 of the lower blade 132. The track 137 has a "T-shape," with a long vertical section represented by 136a and a shorter horizontal section represented by 136b for accepting the linear support member 150.

Figure 6:
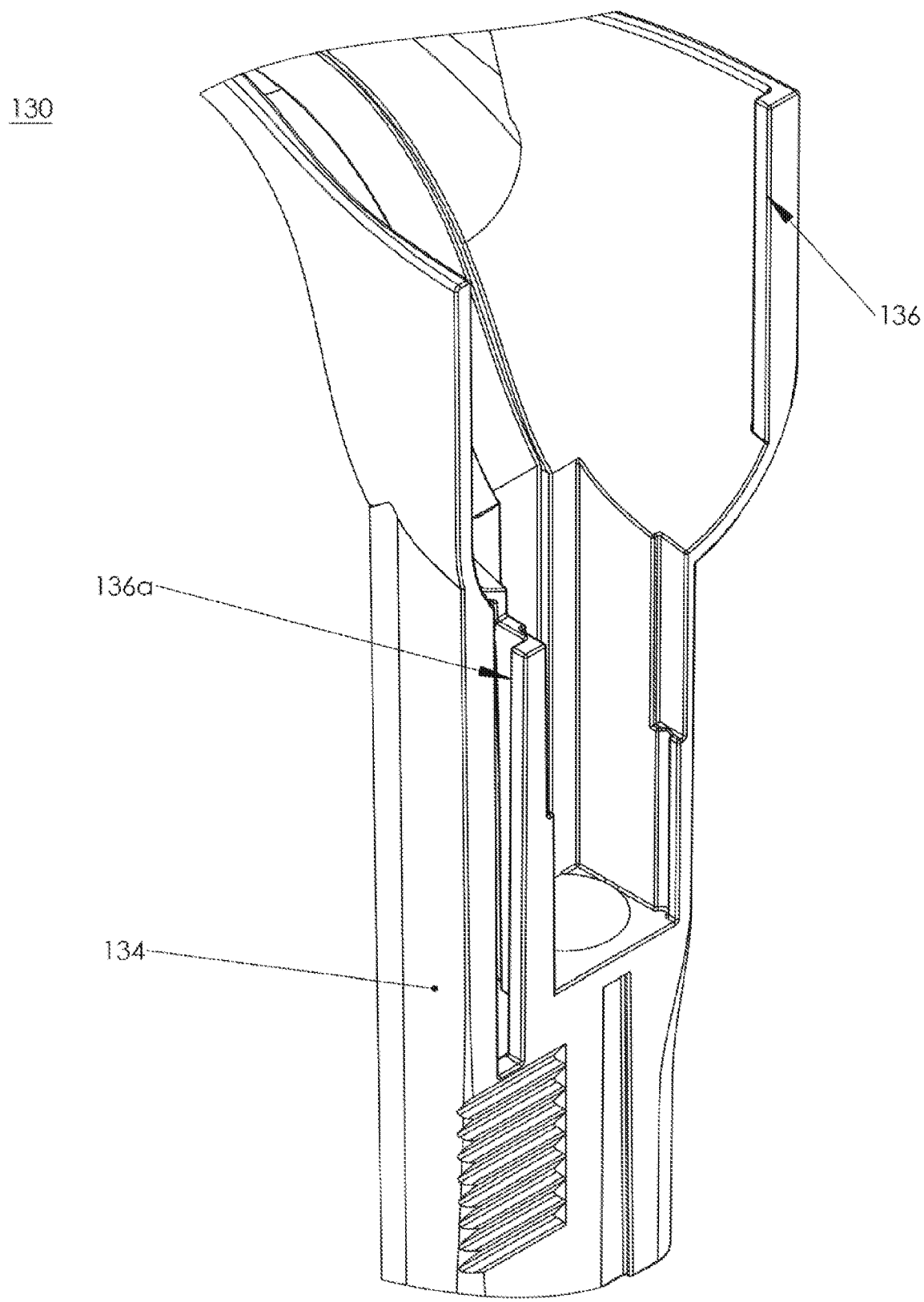
FIG. 6 is a close-up perspective view of the track of FIG. 5.

FIG. 6 shows a close-up perspective view of the track 137 in which the support member 150 rides in.

Figure 7:
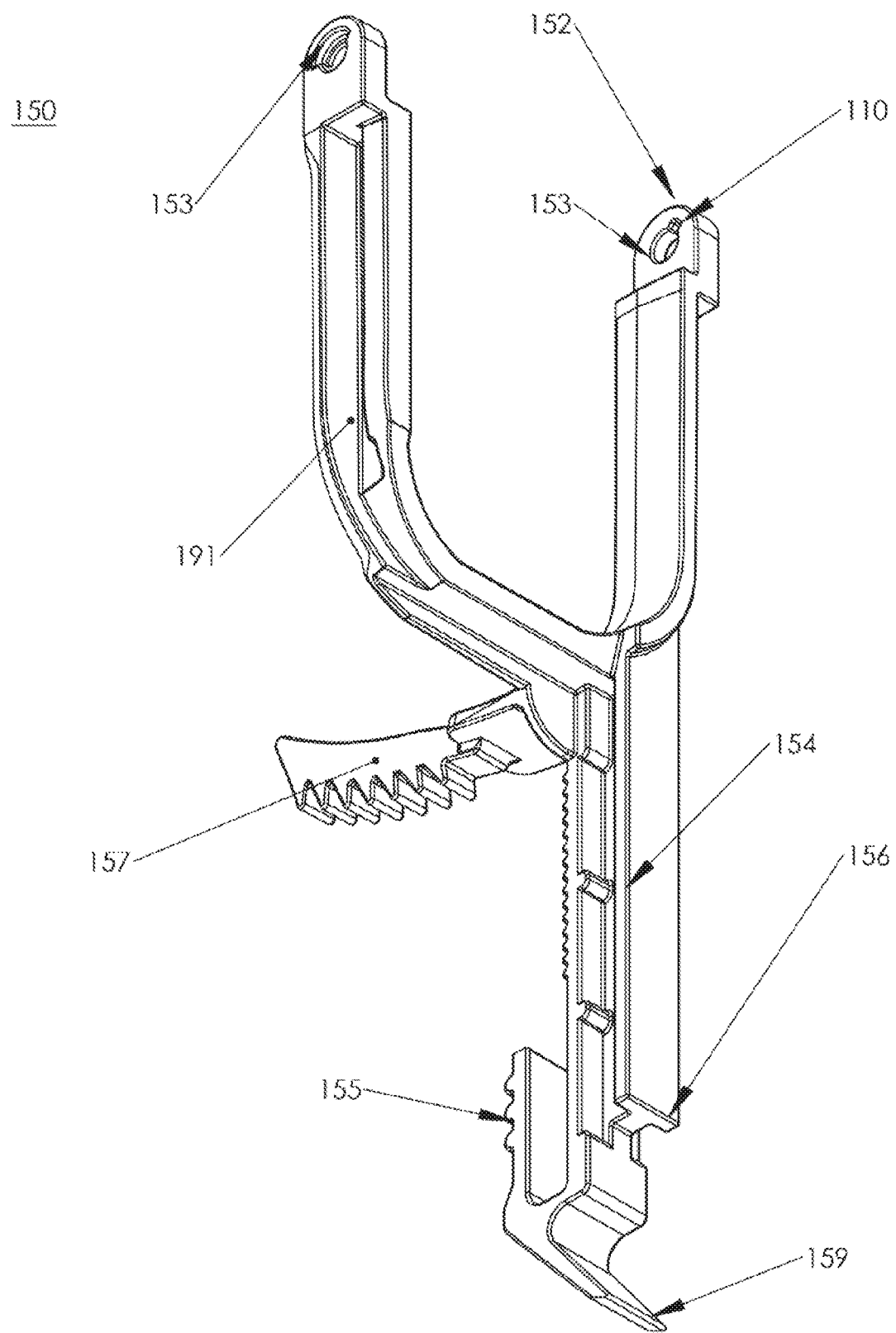
FIG. 7 is a perspective view of a linear support member of the vaginal speculum of FIG. 1A and FIG. 1B.
Figure 8A:
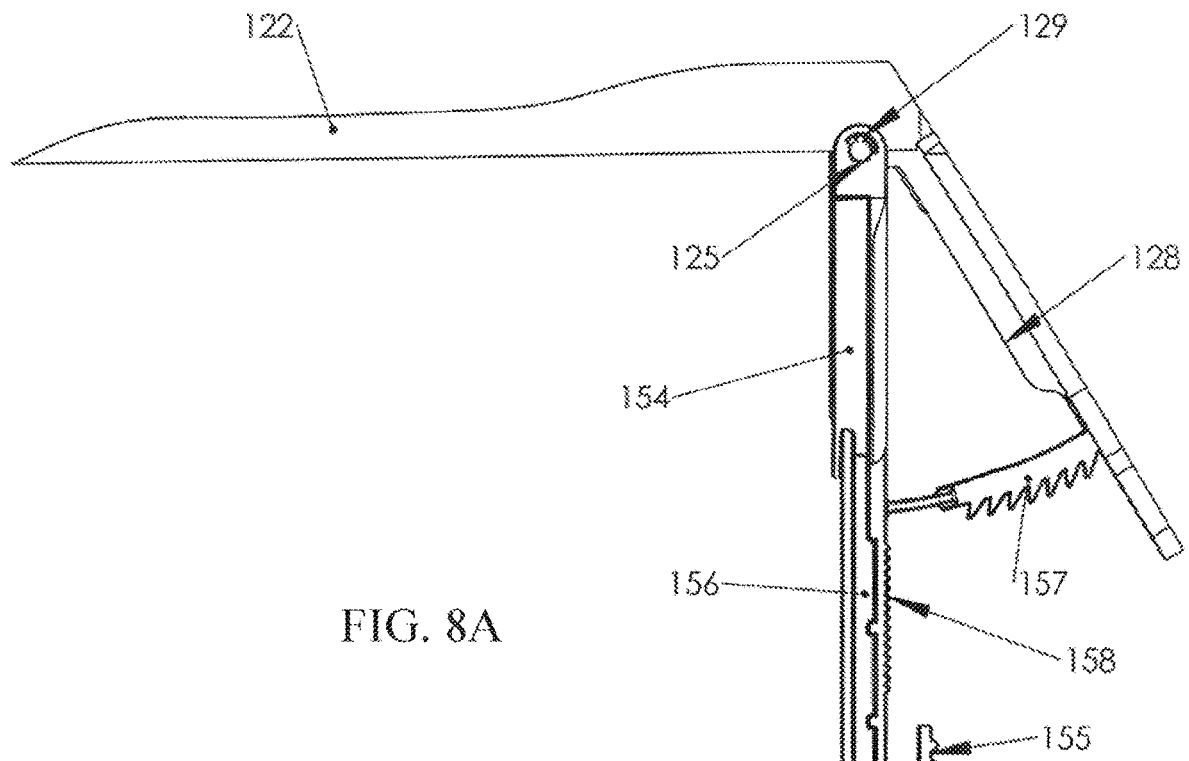
FIG. 8A and FIG. 8B show the upper member of FIG. 1A and FIG. 1B secured to the linear support member of FIG. 7.
Figure 8B:
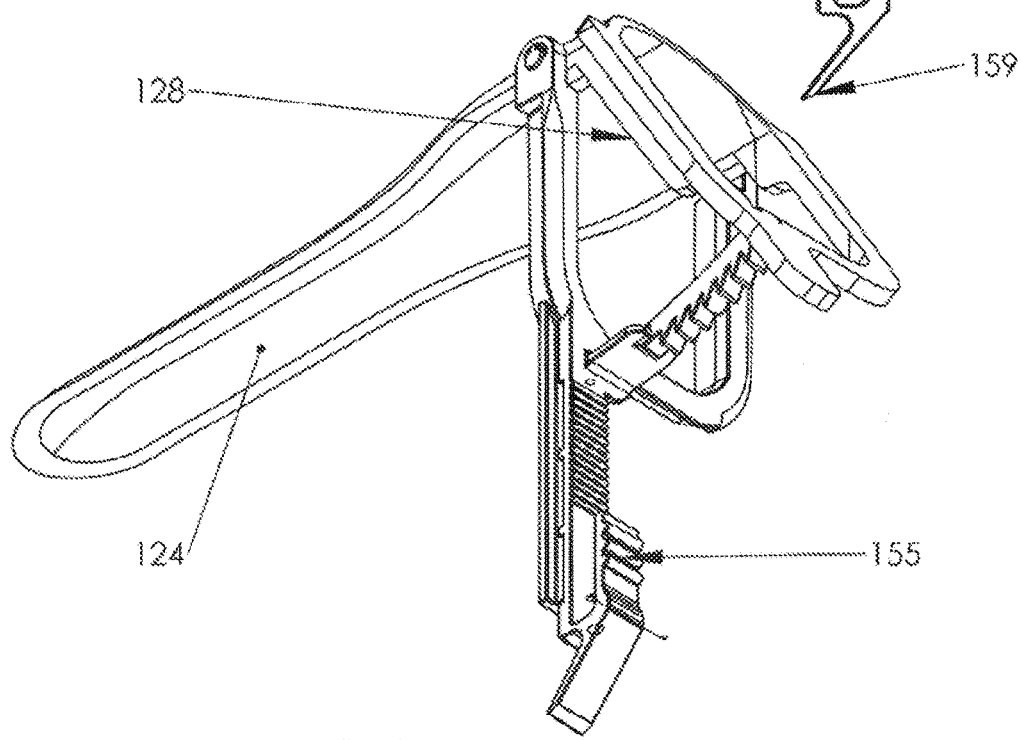
Figure 9:
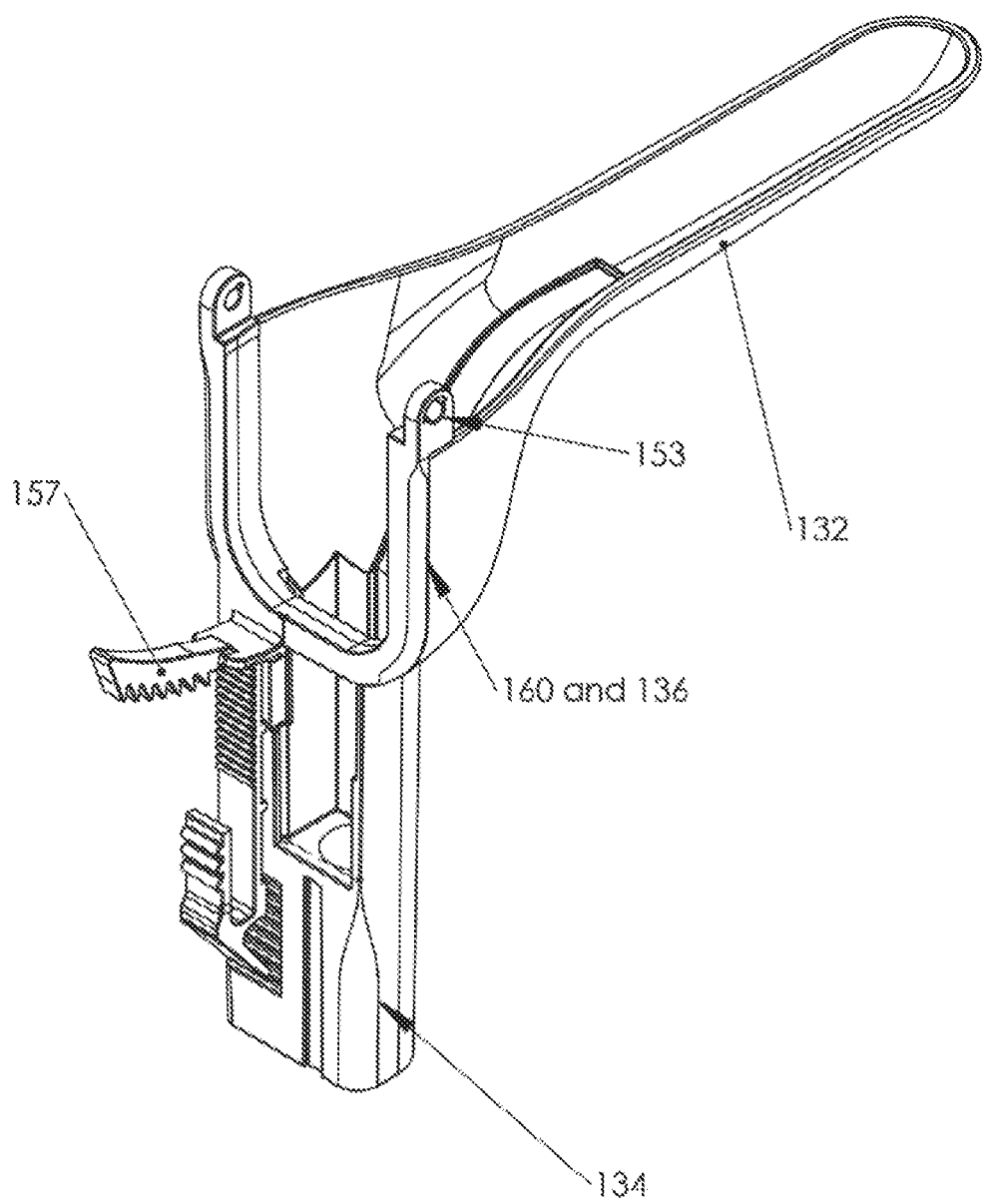
FIG. 9 is a perspective rear view of the linear support member of FIG. 7 positioned within the track of the lower member of FIG. 6.

FIG. 7 in conjunction with FIG. 8A, FIG. 8B and FIG. 9, show various views of the linear support member 150 of the vaginal speculum 100. The linear support member 150 has a proximal end 152, a distal end 156 and an elongated body 154 having a "T-shape." The elongated body 154 rides within the track 137. Additionally, the support structure 136 rides within the hidden slot 191 to provide additional lateral support. Holes 153 of the linear support member 150 attach with the hinge assembly 125 of the upper member 120. Key holes 110 interact with the parallel support beams 129 of the hinge assembly 125 to prevent slippage and subsequent failure of the hinge during lateral stresses. The angulation arm 157 and the elevation leg 155 both protrude from a lip 158 of the elongated body 154. The angulation arm 157 passes through the opening 126 of the operating mechanism 127 of the hinge assembly 125 of the upper member 120 and is held in place with locking teeth on the angulation arm 157. The locking tooth 159 of the elevation leg 155 locks with the stop tabs 131 on the outer surface of the handle 134.

During a gynecological examination or surgical procedure, it is sometimes desirable to illuminate the working area so that a medical professional performing the procedure can properly view the working area. Typical specula are not equipped with illumination devices, and newer speculums that contain light sources generally generate unwanted heat, consume significant power, are tethered to a power source, and project light in unwanted directions. The power consumed requires wires to an external power supply which is cumbersome for a medical practitioner, creates a potential hazard to a patient, and is a source of cross-contamination, as the light source is not easily sterilized between procedures. The unwanted directionality of light will not only illuminate the practitioners working space, but also will illuminate the practitioner and impair the practitioners vision.

Attempts to overcome the above shortcomings have been problematic themselves. One known speculum includes a fiber bundle built into the speculum and an external light source. While this overcomes the heat generation and light directionality problem, the problem for cross-contamination still exists. Another known speculum discloses a light bulb built into the speculum handle with a reflector also built into the handle. While this overcomes the problem of light directionality, problems related to cross-contamination and heat generation still exist. Other speculums disclose a battery operated halogen light source built into the handle. This solves the cross-contamination problem, but does not solve the light directionality problem and heat problem.

FIG. 10A, FIG. 10B, and FIG. 10C, show an embodiment of the built-in light source 160 that resides within the handle 134 of the disposable, plastic speculum 100. An outer housing 163 protects internal batteries 166, a light emitting diode (LED) 164, and internal components of a tab switch 165, which is removed to illuminate the LED 164 when illumination is desired. The LED 164 may produce any desired level of intensity. For example, a resistance tab on the built-in light source 160 may be used to control the intensity of light that the LED 164 can emit. The LED 164 has a high power efficiency and consumes relatively little electrical power with a long lifespan. The LED 164 solves the heat problem because the power efficiency of an LED is greatly superior to prior incandescent or laser solutions. The light output from the LED 164 is highly directional, emitting light only within about a twenty-degree path. This narrow light path ensures that light is only projected onto the working area, and not directly into the practitioner's eyes. The LED 164 is energy-efficient and can be powered by a single lightweight battery 166 or a number of batteries 166. Because the light source 160 is built into the handle 134 of the disposable speculum 100, the problem of cross-contamination is eliminated. The built-in light source 160 also eliminates cumbersome and potentially dangerous wires extending from the speculum 100 to an external power supply.

In an embodiment, the LED light source 164 is a white LED.

In an embodiment, single or multiple wavelength LED sources can be substituted to choose a light wavelength that is uniquely suited to materials, chemicals, tissue, or tools used in current or future gynecological procedures such that these materials, chemicals, tissue or tools will distinctly illuminate when such wavelengths are projected, thus aiding in the practitioner's ability to view and perform a procedure, aiding in material property changes (such as epoxy hardening or activating some other specific material property), altering the state of tissue life, or serving as a contamination neutralizing agent.

In an embodiment, the LED light source 164 is a single wavelength light emitting diode.

In an embodiment, the LED light source 164 is a multiple wavelength light emitting diode.

Figure 11:
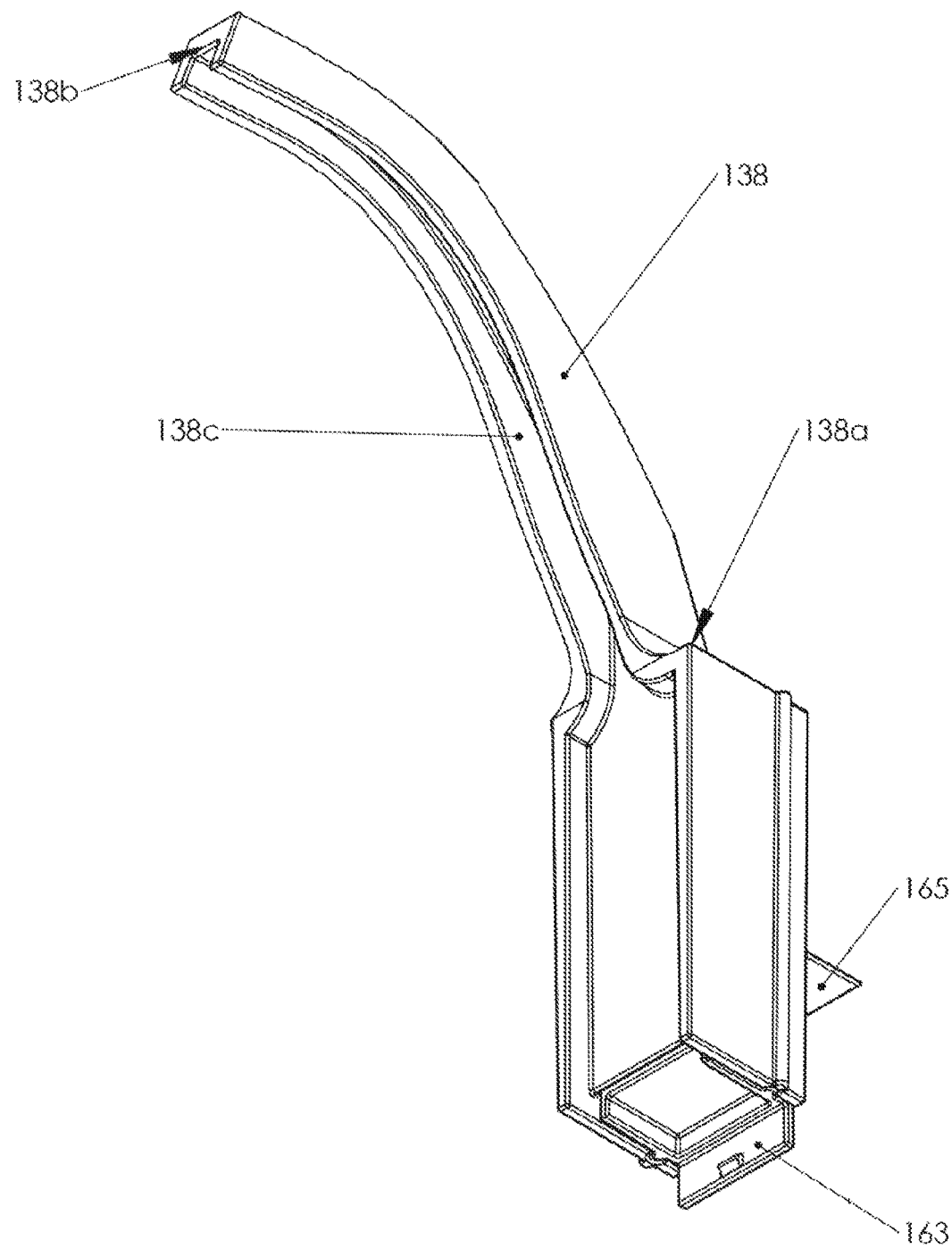
FIG. 11 shows an embodiment of a light guide and smoke evacuation channel for use with the vaginal speculum of FIG. 1A and FIG. 1B having the light source of FIG. 10A.

FIG. 11 shows an embodiment of a light guide 138 having a proximal end 138a and a distal end 138b. The light guide 138 runs from a distal end of the cavity 139 to a distal end of the lower blade 132 on the interior surface 133 of the lower blade 132 (see FIG. 4A and FIG. 4B). The proximal end 138a of the light guide 138 will transfer light coming from the light source 160 through the light guide 138 and out of the distal end 138b. The light guide 138 is contoured to ride on the interior surface 133 of the lower blade 132. The proximal end 138a of the light guide 138 may include a lens that couples with the light source 160 contained in the cavity 139 of the handle 134.

In certain gynecological procedures, it is desirable to remove abnormal cells from the internal and external portions of the cervix. Also, certain gynecological procedures use instruments that produce smoke, which makes it difficult for a medical professional to see a working space during the procedure. Therefore, the use of an external vacuum source during gynecological procedures is common. These external vacuum sources are cumbersome, difficult to manipulate during the procedure, and are a source of cross-contamination, since the vacuum is re-used for many patients.

Existing specula containing both a light guide and a smoke evacuation channel have typically built the light guide into the lower blade thereof and the smoke evacuation channel into the upper blade thereof. This arrangement significantly detracts from the working space between the two blades that is needed to perform vaginal or uterine procedures. Additionally, an external suction tube must be connected to the upper blade of these existing specula which further complicates and obstructs the working area for the physician.

Figure 12:
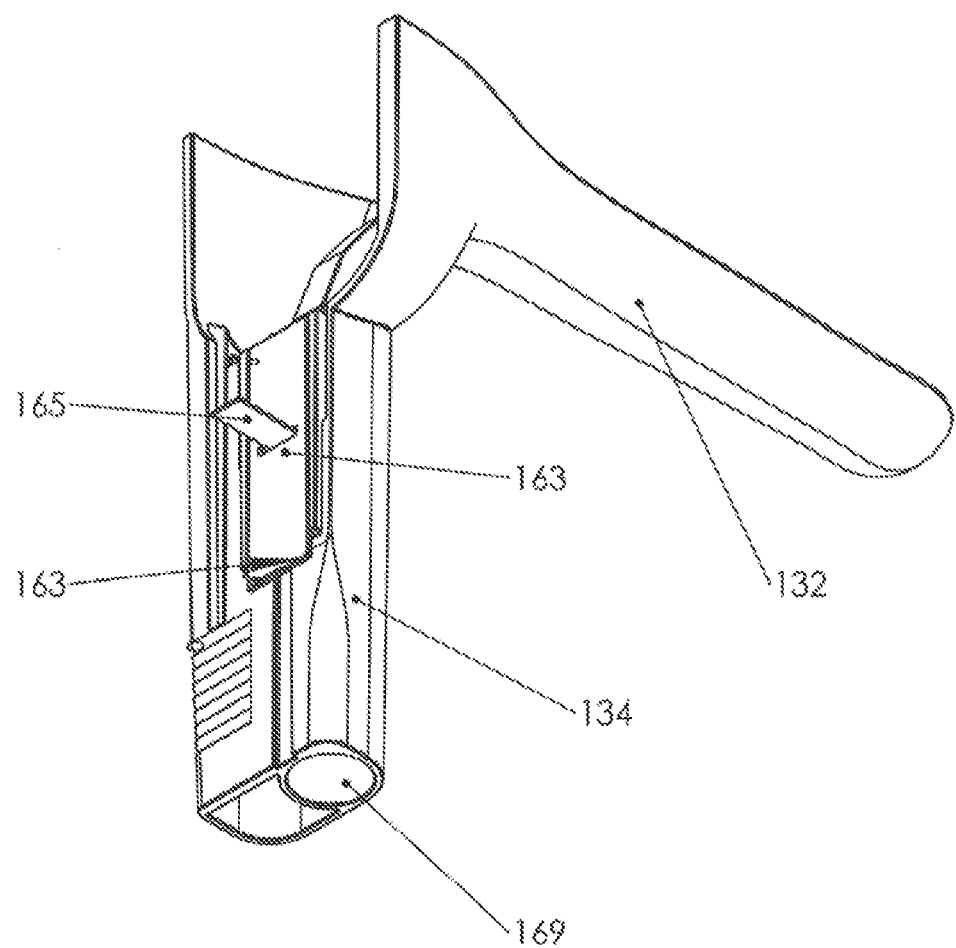
FIG. 12 shows a rear perspective view of the lower member of the vaginal speculum of FIG. 1 having the light source of FIG. 10A.

FIG. 11 in conjunction with FIG. 4A and FIG. 12 shows the lower member 130 of the speculum 100 having a smoke vacuum channel 138c and the light guide 138 merged together and positioned within a sunken relief 135 of the lower member 130 to create a compact structure. The combined smoke channel light guide consists of the light guide 138 with the channel 138c for smoke evacuation cut into the side of the light guide 138 that comes in contact with the lower blade 132. A tunnel formed by the channel 138c is used as a smoke channel. The resulting compact structure created by merging the smoke vacuum channel 138c and the light guide 138 allows for the working space of the speculum 100 to be maximized. Additionally, an external suction tube may be connected to the handle 134 of the speculum 100 at an opening 169 instead of at the upper blade 122 of the speculum 100. Connection of the external suction tube to the lower handle 134 maintains a clear and unobstructed access to the vaginal area for the physician. Smoke is drawn from the distal end 138b of the light guide 138 through the channel 138c that extends under the light guide 138 and out the bottom of the speculum handle 134 where external suction tubing can be attached.

In an embodiment, debris is drawn from the distal end 138b of the light guide 138 through the channel 138c that extends under the light guide 138 and out the bottom of the speculum handle 134 where external suction tubing can be attached.

In an embodiment, bodily fluids are drawn from the distal end 138b of the light guide 138 through the channel 138c that extends under the light guide and out the bottom of the speculum handle 134 where external suction tubing can be attached.

The ability of the speculum 100 of the present disclosure to withstand applied loads is a result of a combination of components of the speculum 100, including, but not limited to, the geometry of the hinge assembly 125, a support beam 128, the parallel support beams 129, the geometry of the upper blade 122 and the lower blade 132, the lateral support structure 136 and the hidden slot 191, and the interdependent loading between the various components. In an embodiment, during use, pressure exerted on the operating mechanism 127 is transferred to the hinge assembly 125, the mechanical holes 153, and down the elongated body 154 of the linear support member 150. As shown clearly in FIG. 3 and FIG.

8, the operating mechanism 127 is an extension of the hinge assembly 125, extending outwards and downwards at an angle. This extension design of the operating mechanism 127 imparts asymmetrical loads on the plastic linear support member 150 and will create lateral movement on the distal end of the upper blade 122. To prevent lateral movement, the novel features of the lateral support structure 136 and the hidden slot 191 have been added. For example, the operating mechanism 127 is capable of absorbing some of the initial load that a user imparts on the speculum 100, such that the load is felt asymmetrically at the two support holes 153 of linear support member 150. These asymmetric loads placed on the linear support member 150 are directed in both a downward and forward direction. The asymmetrical forward loads in turn result in a lateral force on the elongated body 156 of the linear support member 150. In a typical speculum this lateral force will cause twisting of the elongated body of the linear support member thereof, and may cause unwanted movement of the speculum blades or hinge failure. In this embodiment, the lateral support structure 136 and the hidden slot 191 absorb the asymmetrical forward forces and in turn substantially eliminate twisting of the elongated body 156 of the linear support member 150. This reduction in twisting load at the linear support member 150 reduces the tendency of the linear support member 150 to twist and permits the use of a plastic linear support member 150.

During use of the speculum 100, for example during a gynecological procedure, the speculum 100 is inserted into a patient's vagina. The vaginal walls in turn exert a pressure, or load, on the upper blade 122 and the lower blade 132 of the speculum 100. The upper blade 122 and the lower blade 132 are capable of transferring this load to the support member 150 and the operating mechanism 127 because of the unique design of the lateral support structure 136 of the lower member 130 of the speculum 100. The support structure 136 is capable of supporting the lateral load and distributes the vertical load equally down both the linear support member 150 and the operating mechanism 127. This results in a great deal of holding power in a relatively small area without lateral top blade movement or top blade hinge failure.

The upper blade 122 and the lower blade 132 have a curved shape which increases the stiffness and strength of the blades. The stiffness imparted on the curved blades enables the blades to support the applied load along an entire length of the blades, without the need for additional strengthening structures within the blades. The proximal end 152 of the linear support member 150 and the parallel hidden slot 191 and track 137 help prevent failure of the speculum 100 due to asymmetric loading on the blades that would cause the speculum 100 to twist relative to the handle's 134 axis. The design of the speculum 100 prevents twisting.

To operate the speculum 100 of the present disclosure during a gynecological procedure, the upper blade 122 and the lower blade 132 are inserted into a vagina of a patient in a closed position. Closed position can refer to complete closure, where the upper blade 122 engages the lower blade 132, or can refer to partial closure, where the upper blade 122 and the lower blade 132 are partially separated. Thereupon, the linear support member 150 is moved upwardly by pressing on the elevation leg 155 until a desired degree of opening has been attained. The locking tooth 159 of the elevation leg 155 locks with the stop tabs 131 on the outer surface of the handle 134. In an embodiment, when the desired degree of opening has been attained, the operating arm 127 of the operating mechanism 125 is pressed spreading the upper blade 122 and the lower blade 132 apart at an angle. The locking teeth on the angulation arm 157 lock at the opening 126 of the operating mechanism 125, resulting in the speculum 100 being held in the open position. The light source 160 may be turned on to illuminate a surgical or examination site. The pull tab 165 of the light source 160 is removed, resulting in the LED 164 illuminating. At the end of the procedure, the pull tab 165 may be inserted again to turn the LED 16 off. It is to be understood that a speculum 100 of the present disclosure may be fabricated in various sizes, such that the proper sized speculum 100 can be used for each patient. The speculum 100 may also be fabricated from various strength plastic materials based on the desired use of the speculum 100, as long as the structural integrity of the speculum 100 remains. For example, for a routine PAP test, a lower strength speculum 100 may be used as compared to a speculum 100 for use during vaginal hysterectomy.

In an embodiment, a speculum 100 is provided that includes an adjustable upper blade 122 and an adjustable lower blade 132 capable of expanding during use of the speculum 100. Means for providing adjustable blades include, but are not limited to, the use of laterally adjusting blades that expand the width of the blades and the use of longitudinally adjustable blades that expand the length of the blades. The adjustable blades can be withdrawn partially or completely.

In an embodiment, a speculum 100 is provided that includes heating means for warming the upper blade 122 or the lower blade 132. The extra warmth provided by the heating means enhances patient comfort and helps to relax the vaginal area. Means for heating the blades include, but are not limited to, the use of heating coils within a hollowed out space of the blades, the use of powdered chemicals within a hollowed out space of the blades that are able to oxidize when exposed to air. In an embodiment, a speculum 100 includes heating coils on the upper blade 122 and the lower blade 132 for bringing the temperature of the blades to body temperature. In an embodiment, the heating coils can be powered by the batteries 166 used in the built-in light source 160. In an embodiment, the heating coils can be powered by a different battery.

In an embodiment, a speculum 100 is provided that includes a distally mounted camera chip for real-time data capture and/or viewing of a medical procedure. The camera chip can store and/or capture data, and communicate with computer software to analyze the data. Data captured on the camera chip can be analyzed for cellular and visual abnormalities of the vulva, vagina and cervix.

In an embodiment, a speculum 100 is provided that includes a pressure gauge, so that the pressure being applied from the speculum 100 to the vagina, or from the vagina to the speculum 100, can be monitored, as well as the tightness of the vaginal canal. The pressure gauge may be similar to a strain gauge and may be built into the speculum 100, for example, at the hinge assembly 125.

In an embodiment, a speculum 100 is provided that includes a pH test strip or a pH meter, for the fast and accurate determination of the acidity level of the vaginal canal being examined. The pH strip or pH meter would be exposed to vaginal secretions to access the pH at any point in a gynecological or surgical procedure.

In an embodiment, a speculum 100 is provided that includes means for lubricating either or both of the upper blade 122 and the lower blade 132. The lubricated blades make it easy for the speculum 100 to be inserted into a vaginal cavity of a patient, while providing a moist work environment during a gynecological or surgical procedure.

In an embodiment, a body of the upper blade 122 and/or the lower blade 132 has a hollowed-out space for passage of a lubricating jelly, as well as holes at a surface for release of the lubricating jelly.

In an embodiment, the speculum 100 may come pre-packaged with an amount of lubricating jelly within the hollowed-out space of the blade. The lubricating jelly is released through the holes present at the blades surface, for example, by pushing a button on the handle 134. In an embodiment, the speculum 100 may include a port that can attach to a luer-lock syringe having the lubricating jelly, for passage of the lubricating jelly into the blades.

A method for dilating a vagina includes providing a disposable vaginal speculum. The speculum has an upper member containing an upper blade, a lower member containing a lower blade and including one or more lateral support beams that extend downward from an interior side of the lower blade, and a linear support member that connects the upper member having the upper blade to the lower member containing the lower blade, such that the linear support member engages the lateral support beam or beams and engages a rotational operating mechanism extending off the upper blade and a linear operating mechanism extending from the lower member. The linear support member is vertically moveable within a track positioned at a single side of a handle portion of the lower member. The method for dilating a vagina further includes inserting the upper blade and the lower blade of the speculum into an opening of the vagina, and creating a working space between the upper blade and the lower blade, thus dilating the vagina.

Figure 13:
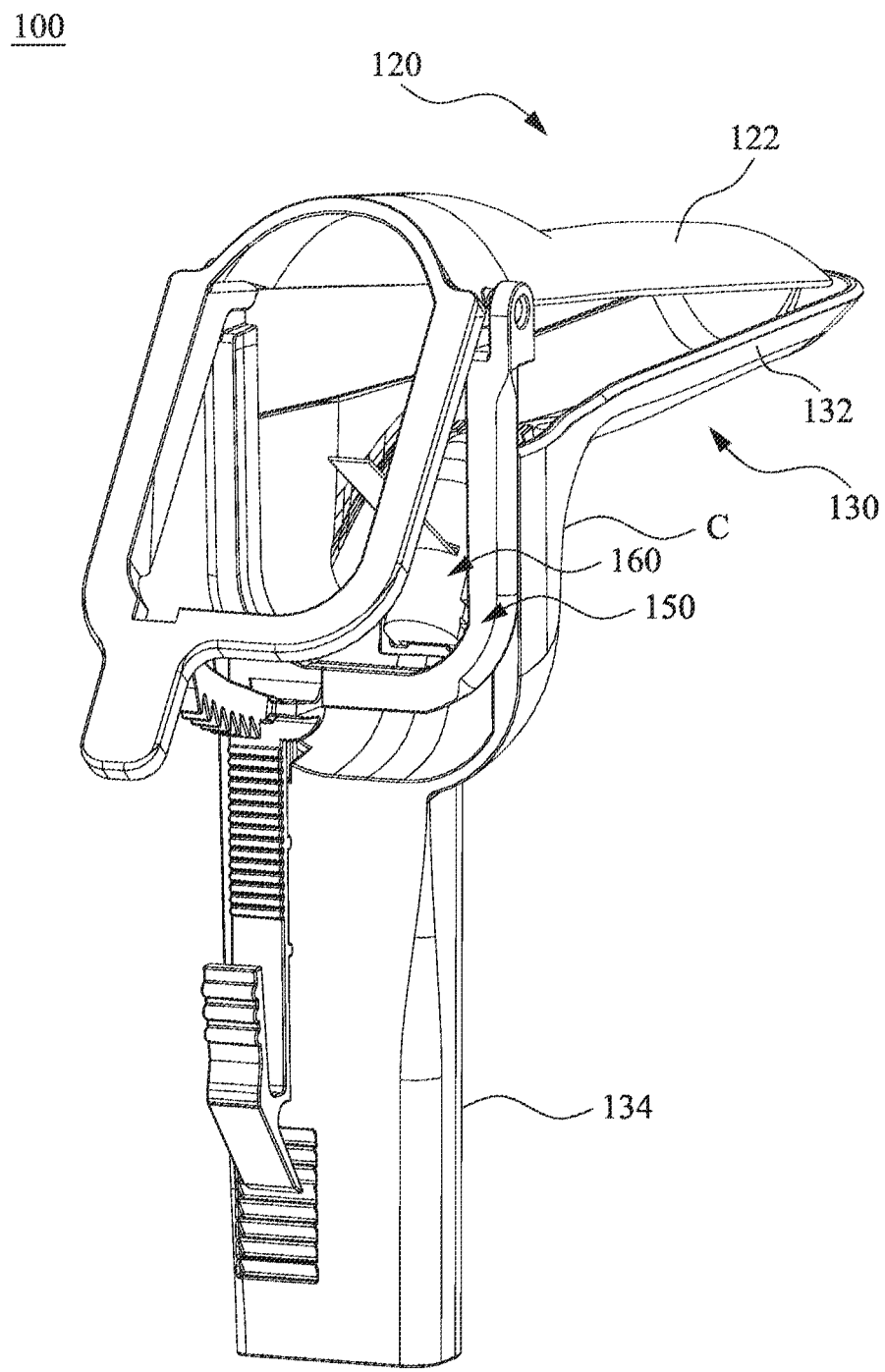
FIG. 13 is a perspective rear view of a speculum according to another embodiment of the present disclosure.
Figure 14:
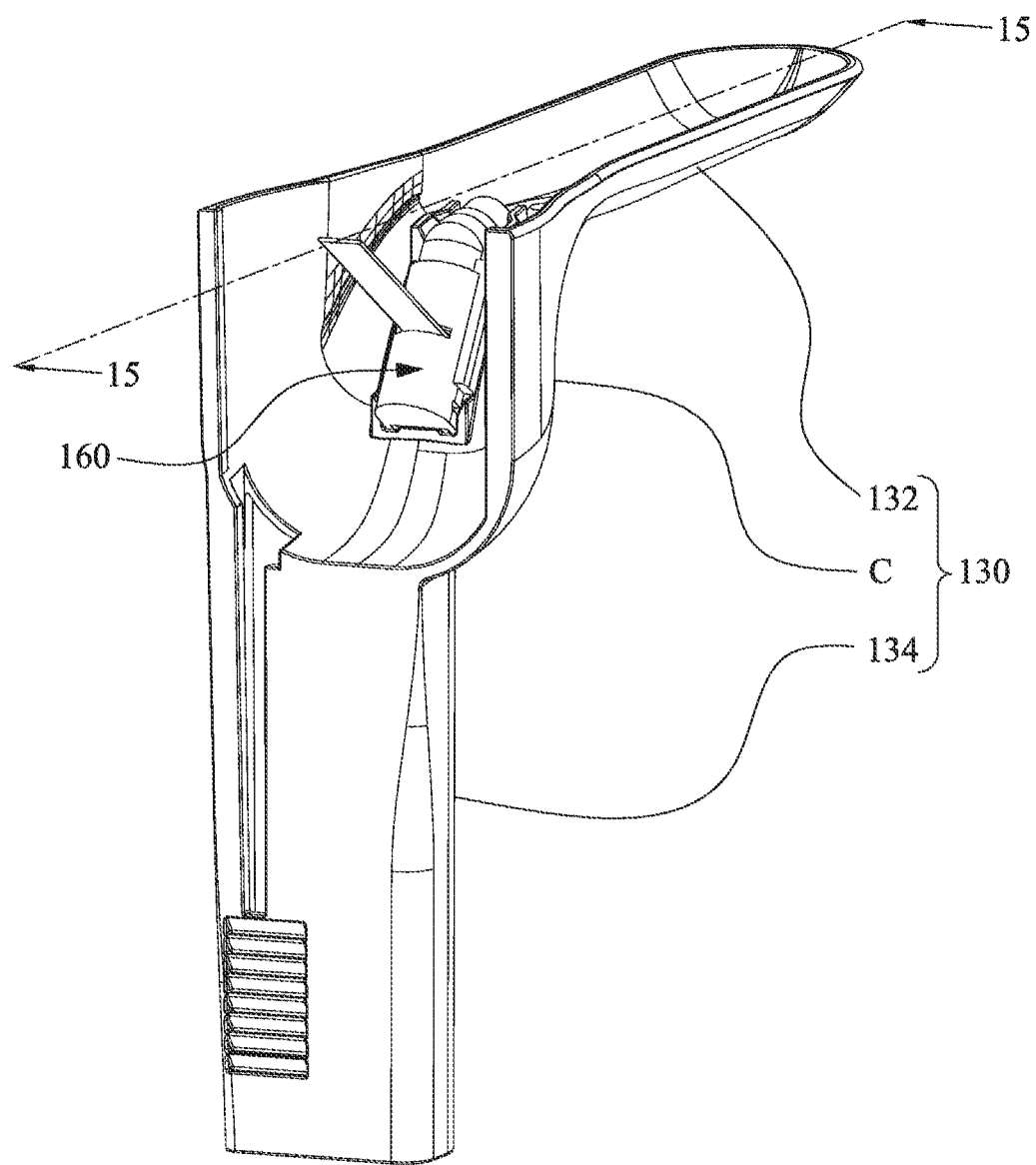
FIG. 14 is a perspective rear view of the lower member and the light source of FIG. 13.
Figure 15:
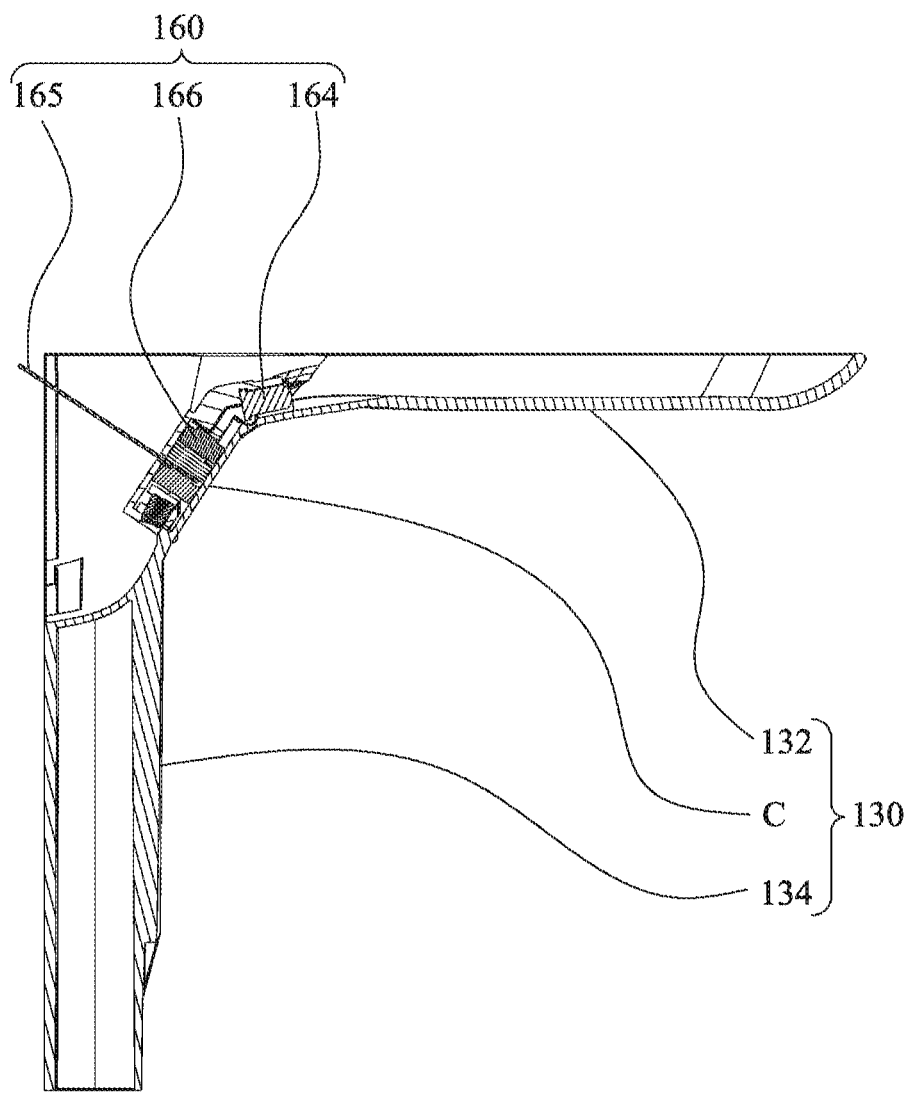
FIG. 15 is a sectional view taken along line 15 of FIG. 14.

FIG. 13 is a perspective rear view of a speculum 100 according to another embodiment of the present disclosure. FIG. 14 is a perspective rear view of the lower member 130 and the light source 160 of FIG. 13. FIG. 15 is a sectional view taken along line 15 of FIG. 14. As shown in FIGS. 13-15, the speculum 100 includes an upper member 120, a lower member 130, a linear support member 150, and a light source 160. The upper member 120 has an upper blade 122. The lower member 130 has a lower blade 132 and a handle portion 134. The handle portion 134 is connected to the lower blade 132. The linear support member 150 connects the upper member 120 and the lower member 130 to allow the upper blade 122 and the lower blade 132 to move between an open state and a close state. The light source 160 is disposed on the junction of the lower blade 132 and the handle portion 134.

In some embodiments, the lower member 130 includes a curved portion C. The curved portion C connects the lower blade 132 and the handle portion 134. The light source 160 is disposed on the curved portion C.

As shown in FIGS. 13-15, a space is defined between the upper blade 122 and the lower blade 132. The light source 160 is configured to provide light to the space. More specifically, the light source 160 includes at least one lamp disposed on the curved portion C. The lamp has a light output surface facing the space. The lamp is, for example, an LED 164.

Since the light source 160 is disposed on the curved portion C and is configured to directly provide light to the space, the light guide for transferring light from the light source 160 to the space can be eliminated, resulting in a much brighter light. Furthermore, the light source 160 is built into the curved portion C so that the light source 160 maintains a low profile and does not obstruct operator visibility.

As shown in FIGS. 13-15, the light source 160 further includes at least one energy storage device. The energy storage device is, for example, at least one battery 166. The battery (or batteries) 166 is disposed on the curved portion C and is configured to provide a supply of energy for the LED 164.

Conventional light sources for speculums are re-usable. Re-usable light sources increase cross-contamination risks and are of significant concern to hospitals. Unlike conventional light sources for speculums, the entire speculum 100 of FIGS. 13-15 including the light source 160 is designed for a single use. Specifically, since both the LED 164 and the battery (or batteries) 166 are disposed on the curved portion C, wires connecting the LED 164 and the battery (or batteries) 166 can be short and inexpensive to build. Furthermore, the light source 160 is permanently fixed to the curved portion C. That is, the user cannot easily separate the light source 160 from the curved portion C, and therefore the user tends to discard the light source 160 along with the speculum 100. In addition, the battery (or batteries) 166 of the light source 160 contains only enough energy for a single use of the speculum 100, further discouraging the user from re-using the light source 160.

In some embodiments, the light source 160 includes a tab switch 165. The tab switch 165 electrically separates the battery (or batteries) 166 and the LED 164. The tab switch 165 is removable. The battery (or batteries) 166 powers the LED 164 to illuminate when the user removes the tab switch 165.

In some embodiments, the battery (or batteries) 166 is disposed between the LED 164 and the handle portion 134 so that the battery (or batteries) 166 does not obstruct the light provided by the LED 164.

Other details regarding the speculum 100 of FIGS. 13-15 are similar to the speculum 100 of FIGS. 1-12 and therefore are not repeated here to avoid duplicity.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A speculum comprising:
   a member comprising:
      a handle extending in a first longitudinal direction,
      a first blade extending distally with respect to the handle in a second longitudinal direction, and
      a portion extending between the handle and the first blade, wherein the portion comprises a bottom wall extending in a third longitudinal direction of the portion and comprises sidewalls extending from the bottom wall, wherein the third longitudinal direction is different from the first longitudinal direction and the second longitudinal direction;
   a second blade coupled to the member; and
   a light emitting diode (LED) positioned adjacent a distal end of the portion for emitting light distally into a space between the first and second blades.

2. The speculum of claim 1, further comprising a power source positioned on the bottom wall of the portion such that the power source extends along the third longitudinal direction.

3. The speculum of claim 2, further comprising an assembly that comprises the power source and the LED.

4. The speculum of claim 3, wherein the LED defines a distal end of the assembly.

5. The speculum of claim 3, wherein a proximal end of the assembly is positioned on the bottom wall of the portion.

6. The speculum of claim 3, wherein the assembly does not extend along the handle.

7. The speculum of claim 3, wherein the assembly further comprises a tab switch that electrically separates the power source from the LED prior to use of the speculum.

8. The speculum of claim 7, wherein the tab switch extends substantially perpendicularly with respect to the portion.

9. The speculum of claim 3, wherein the assembly is built into the portion.

10. The speculum of claim 1, wherein the portion comprises a curved surface.

11. The speculum of claim 1, wherein the handle, the portion, and the first blade are integrally formed as one structure.

12. The speculum of claim 1, wherein, when the speculum is in a closed state, the second blade is rotatable away from the first blade to adjust the speculum to an open state.

13. The speculum of claim 12, wherein, when the speculum is in the open state, the second blade is rotatable towards the first blade to adjust the speculum to a closed state.

14. The speculum of claim 1, further comprising one or more locking teeth by which the second blade can be locked at a selected position with respect to the first blade.

15. The speculum of claim 1, wherein the LED is positioned to emit light directly into the space between the first and second blades.

16. The speculum of claim 1, wherein the LED substantially faces a distal end of the first blade.

17. A method of operating a speculum, the method comprising:
   inserting a first blade and a second blade of the speculum into a patient, the speculum comprising a member to which the second blade is coupled, and the member comprising:
      a handle extending in a first longitudinal direction,
      the first blade, extending distally with respect to the handle in a second longitudinal direction, and
      a portion extending between the handle and the first blade, wherein the portion comprises a bottom wall extending in a third longitudinal direction of the portion and comprises sidewalls extending from the bottom wall, wherein the third longitudinal direction is different from the first longitudinal direction and the second longitudinal direction; and
   emitting light distally into a space between the first and second blades from a light emitting diode (LED) positioned adjacent a distal end of the portion.

18. The method of claim 17, further comprising powering the LED with a power source, wherein the power source is positioned on the bottom wall of the portion such that the power source extends along the third longitudinal direction.

19. The method of claim 18, wherein the speculum further comprises an assembly that comprises the power source and the LED.

20. The method of claim 19, wherein the LED defines a distal end of the assembly.

21. The method of claim 19, wherein a proximal end of the assembly is positioned on the bottom wall of the portion.

22. The method of claim 19, wherein the assembly does not extend along the handle.

23. The method of claim 19, wherein the assembly further comprises a tab switch, and wherein the method further comprises electrically connecting the power source to the LED upon removal of the tab switch from the assembly.

24. The method of claim 23, wherein the tab switch extends substantially perpendicularly with respect to the portion.

25. The method of claim 19, wherein the assembly is built into the portion.

26. The method of claim 17, wherein the portion comprises a curved surface.

27. The method of claim 17, wherein the handle, the portion, and the first blade are integrally formed as one structure.

28. The method of claim 17, further comprising, when the speculum is in a closed state, rotating the second blade away from the first blade to adjust the speculum to an open state within the patient.

29. The method of claim 28, further comprising, when the speculum is in the open state, rotating the second blade towards the first blade to effect a adjust the speculum to the closed state.

30. The method of claim 17, further comprising locking the second blade at a selected position with respect to the first blade using one or more locking teeth.

31. The method of claim 17, further comprising emitting light directly from the LED into the space between the first and second blades.

32. The method of claim 17, further comprising emitting light into the space prior to inserting the first and second blades into the patient.

33. The method of claim 17, further comprising emitting light into the space after inserting the first and second blades into the patient.

* * * * *

UNITED STATES PATENT AND TRADEMARK OFFICE
CERTIFICATE OF CORRECTION

PATENT NO. : 12,419,510 B2
APPLICATION NO. : 18/225345
DATED : September 23, 2025
INVENTOR(S) : Jeffrey Ralph Swift and Aaron J. Buchok Page 1 of 1

It is certified that error appears in the above-identified patent and that said Letters Patent is hereby corrected as shown below:

In the Claims

Column 14
Line 36, in Claim 29, before "adjust" delete "effect a"

Signed and Sealed this
Twenty-third Day of December, 2025

John A. Squires
*Director of the United States Patent and Trademark Office*